(12) United States Patent
Milenkovic et al.

(10) Patent No.: US 10,370,246 B1
(45) Date of Patent: Aug. 6, 2019

(54) PORTABLE AND LOW-ERROR DNA-BASED DATA STORAGE

(71) Applicant: The Board of Trustees of the University of Illinois, Urbana, IL (US)

(72) Inventors: Olgica Milenkovic, Urbana, IL (US); Ryan Gabrys, San Diego, CA (US); S. M. Hossein Tabatabaei Yazdi, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/789,519

(22) Filed: Oct. 20, 2017

Related U.S. Application Data

(60) Provisional application No. 62/410,559, filed on Oct. 20, 2016.

(51) Int. Cl.
| | |
|---|---|
| *B82Y 10/00* | (2011.01) |
| *G11C 13/02* | (2006.01) |
| *G06N 3/12* | (2006.01) |
| *C12Q 1/68* | (2018.01) |
| *C12Q 1/6806* | (2018.01) |

(52) U.S. Cl.
CPC .............. *B82Y 10/00* (2013.01); *C12Q 1/68* (2013.01); *C12Q 1/6806* (2013.01); *G06N 3/12* (2013.01); *G06N 3/123* (2013.01); *G11C 13/025* (2013.01)

(58) Field of Classification Search
CPC . G06N 3/123; G06N 3/12; C12Q 1/68; C12Q 1/6806
See application file for complete search history.

(56) References Cited

U.S. PATENT DOCUMENTS

| | | | |
|---|---|---|---|
| 6,223,128 B1 * | 4/2001 | Allex ...................... | G06F 19/22 |
| | | | 435/6.12 |
| 9,996,778 B2 * | 6/2018 | Church ................... | G06F 19/22 |
| | (Continued) | | |

FOREIGN PATENT DOCUMENTS

WO    2017/189469    11/2017

OTHER PUBLICATIONS

Milane, I. et al., "Using Tablet for visual exploration of second-generation sequencing data," Brief. Bioinform. vol. 14, 193-202 (2013).

(Continued)

*Primary Examiner* — Vanthu T Nguyen
(74) *Attorney, Agent, or Firm* — McDonnell Boehnen Hulbert & Berghoff LLP

(57) ABSTRACT

The present disclosure provides DNA-based storage system demonstrated through experimental and theoretical verification that such a platform can easily be implemented in practice using portable, nanopore-based sequencers. The gist of the approach is to design an integrated pipeline that encodes data to avoid synthesis and sequencing errors, enables random access through addressing, and leverages efficient portable nanopore sequencing via new anchored iterative alignment and insertion/deletion error-correcting codes. The embodiments herein represent the only known random access DNA-based data storage system that uses error-prone portable, nanopore-based sequencers and produces low-error readouts with the highest reported information rate and density.

20 Claims, 14 Drawing Sheets

Specification includes a Sequence Listing.

(56) References Cited

U.S. PATENT DOCUMENTS

| | | | | |
|---|---|---|---|---|
| 2004/0001371 | A1* | 1/2004 | Mansuripur | B82Y 10/00 365/200 |
| 2005/0053968 | A1* | 3/2005 | Bharadwaj | B82Y 10/00 435/6.12 |
| 2015/0261664 | A1* | 9/2015 | Goldman | G06F 19/22 711/154 |
| 2017/0141793 | A1* | 5/2017 | Strauss | H03M 13/05 |
| 2018/0127804 | A1* | 5/2018 | Dean | C12N 15/1003 |

OTHER PUBLICATIONS

MATLAB source code https://github.com/smhty/MATLAB_MinION (2016).

Dolecek, L. & Anantharam, V., "Repetition error correcting sets: explicit constructions and prefixing methods," SIDMA vol. 23, pp. 2120-2146 (2010).

Molecular facts and figures available at https://www.idtdna.com/pages/docs/educational-resources/molecular-facts-and-figures.pdf?sfvrsn=4 (2016).

Blawat, M. et al., "Forward error correction for DNA data storage," Procedia Compu. Si. vol. 80, pp. 1011-1022 (2016).

Laver, T. et al., "Assessing the performance of the Oxford Nanopore Technologies MinION," BDQ vol. 3, pp. 1-8 (2015).

Gray, J. & Van Ingen, C., "Empirical measurements of disk failure rates and error rates," Preprint at http://arXIV.org/abs/cs/0701166 (2007).

Benenson, Y. et al. "An autonomous molecular computer for logical control of gene expression," Nature vol. 429, pp. 423-429 (May 2004).

Boneh, D. et al. "Breaking DES using a molecular computer," Technical Report CS-TR-489-95, Department of Computer Science, Princeton University (1995).

Braich, R. S. et al. "Solution of a 20-variable 3-SAT problem on a DNA computer," Science vol. 296, pp. 492-502 (Apr. 2002).

Breslauer, K. et al. "Predicting DNA duplex stability from the base sequence," Proc. Natl. Acad. Sci. USA vol. 83, pp. 3746-3750 (1986).

Clote, P. et al. "Computational Molecular Biology—An Introduction," Wiley Series in Mathematical and Computational Biology, New York (2000).

D'yachkov, A. et al. "Exordium for DNA codes," J. Comb. Optim. vol. 7, No. 4, pp. 369-379 (2003).

D'yachkov, A. et al. "New results on DNA codes," Proc. IEEE Int. Symp. Inform. Theory (ISIT'05), Adelaide, Australia, pp. 283-287 (Sep. 2005).

Gaborit, P. et al. "Linear constructions for DNA codes," Theoretical Computer Science vol. 334, No. 1-3, pp. 99-113 (Apr. 2005).

Cooke, C. H. et al. "Polynomial construction of complex Hadamard matrices with cyclic core," Applied Mathematics Letters vol. 12, pp. 87-93 (1999).

King, O. D. "Bounds for DNA codes with constant GC-content," The Electronic Journal of Combinatorics vol. 10, No. 1, #R33 (2003).

Mansuripur, M. et al. "Information storage and retrieval using macromolecules as storage media," University of Arizona Technical Report (2003).

Marathe, A. et al. "On combinatorial DNA word design," J. Comput. Biol. vol. 8, pp. 201-219 (2001).

Mneimneh, S. "Computational Biology Lecture 20: RNA secondary structures," available online at engr.smu.edu/»saad/courses/cse8354/lectures/lecture20.pdf (2004).

Milenkovic, O. "On the generalized Hamming weight enumerators and coset weight distributions of even isodual codes," Proceedings of the 2001 IEEE International Symposium on Information Theory (Jun. 29, 2001).

Milenkovic, O. et al. "DNA codes that avoid secondary structures," Proc. IEEE Int. Symp. Inform. Theory (ISIT'05), Adelaide, Australia, pp. 288-292 (Sep. 2005).

Nussinov, R. et al. "Fast algorithms for predicting the secondary structure of single stranded RNA," Proc. Natl. Acad. Sci. USA vol. 77, No. 11, pp. 6309-6313 (1980).

Rykov, V. et al. "DNA sequences and quaternary cyclic codes," Proc. IEEE Int. Symp. Inform. Theory (ISIT'01), Washington DC, p. 248 (Jun. 2001).

Stojanovic, M. N. et al. "A deoxyribozyme-based molecular automaton," Nature Biotechnology vol. 21, pp. 1069-1074 (2003).

SvanstrÄom, M. et al. "Bounds and constructions for ternary constant-composition codes," IEEE Trans. Inform. Theory vol. 48, No. 1, pp. 101-111 (Jan. 2002).

Tsaftaris, S. et al. "DNA computing from a signal processing viewpoint," IEEE Signal Processing Magazine, pp. 100-106 (Sep. 2004).

Tzeng, K. K. et al. "On extending Goppa codes to cyclic codes," IEEE Trans. Inform. Theory vol. IT-21, pp. 712-716 (Nov. 1975).

Winfree, E. "DNA computing by self-assembly," The Bridge vol. 33, No. 4, pp. 31-38 (2003) Also available online at http://www.dna.caltech.edu/Papers/FOE 2003 final.pdf.

Zuker, M. "Mfold web server for nucleic acid folding and hybridization prediction," Nucleic Acids Res. vol. 31, No. 13, pp. 3406-3415 (2003) Web access at http://www.bioinfo.rpi.edu/»zukerm/ma/.

Gabrys, R. et al. "Codes in the Damerau Distance for Deletion and Adjacent Transposition Correction" arXiv:1601.06885, published to arxiv.org on Sep. 6, 2016.

Bajic, D. et al. "A simple suboptimal construction of cross-bifix-free codes" Cryptography and Communications archive 6:27-37 (Aug. 8, 2013).

Baldoni, V. et al. "A user's guide for LattE integrale v1.7.2" retrieved from https://www.math.ucdavis.edu/~latte/software/packages/latte_current/manual_v1.7.2.pdf on Mar. 8, 2017 (Oct. 2014).

Abualrub, T. et al. "Construction of cyclic codes over GF(4) for DNA computing" Journal of the Franklin Institute, 343, pp. 448-457 (2006).

Wood, D. H. "Applying error correcting codes to DNA computing (Abstract)" Proceedings of the 4th DIMACS International Meeting on DNA Based Computing, pp. 109-110 (1998).

Hagiwara, M. "A short proof for the multi-deletion error correction property of Heiberg codes," IEICE Communications Express vol. 5, No. 2, pp. 49-51 (Jan. 25, 2016).

Milenkovic, O. et al. "On the design of codes for DNA computing" Coding and Cryptography International Workshop, Revised Selected Papers, pp. 100-119 (Mar. 14-18, 2005).

Hall, J. I. "Notes on Coding Theory (Chapter 5—Generalized Reed-Solomon Codes)" Department of Mathematics, Michigan State University available online at http://users.math.msu.edu/users/jhall/classes/codenotes/coding-notes.html (Jan. 7, 2015 revision).

Hall, J. I. "Notes on Coding Theory (Chapter 6—Modifying Codes)" Department of Mathematics, Michigan State University available online at http://users.math.msu.edu/users/jhall/classes/codenotes/coding-notes.html (Jan. 7, 2015 revision).

Hall, J. I. "Notes on Coding Theory (Chapter 7—Codes over Subfields)" Department of Mathematics, Michigan State University available online at http://users.math.msu.edu/users/jhall/classes/codenotes/coding-notes.html (Jan. 7, 2015 revision).

Hall, J. I. "Notes on Coding Theory (Chapter 8—Cyclic Codes)" Department of Mathematics, Michigan State University available online at http://users.math.msu.edu/users/jhall/classes/codenotes/coding-notes.html (Jan. 7, 2015 revision).

Hall, J. I. "Notes on Coding Theory (Chapter 9—Weight and Distance Enumeration)" Department of Mathematics, Michigan State University available online at http://users.math.msu.edu/users/jhall/classes/codenotes/coding-notes.html (Jan. 7, 2015 revision).

Zhirnov, V. et al. "Nucleic acid memory," Nat. Mater. vol. 15, pp. 366-370 (2016).

Goda, K. & Masaru, K. "The history of storage systems," IEEE vol. 100, pp. 1433-1440 (2012).

Laure, C., et al., "Coding in 2D: using intentional disperity to enhance the information capacity of sequence-coded polymer barcodes," Angew. Chem. vol. 128, pp. 10880-10883 (2016).

Erlich, Y. & Zielinski, D., "Capacity-approaching DNA storage," preprint available at http://dx.doi.org/10.1101/074237 (2016).

(56) References Cited

OTHER PUBLICATIONS

Steinbock, J. et al., "Probing the size of proteins with glass nanopores," Nanoscale vol. 6, pp. 14380-14387 (2014).
Edgar, R. C., MUSCLE: multiple sequence alignment with high accuracy and high throughput, Nucleic Acids Res. vol. 32, pp. 1792-1797 (2004).
Kim, J. & Ma, J., "PSAR-Align: improving multiple sequence alignment using probabilistic sampling," Bioinformatics vol. 30, pp. 1010-1012 (2013).
Li, H. & Durbin, R., "Fast and accurate short read alignment with Burrows-Wheeler Transform," Bioinformatics vol. 25, pp. 1754-1760 (1992).
Wallace, G. K., "The JPEG still picture compression standard," IEEE Transactions on Consumer Electronics vol. 38, pp. 18-34 (1992).
Josefsson, S., "The Base16, Base32, and Base64 data encodings," IETF (2006).
Batu, T., et al., "Reconstructing strings from random traces," SODA vol. 15, pp. 910-918 (2004).
Holenstein, T., et al., "Trace reconstruction with constant deletion probability and related results," SODA vol. 19, pp. 389-398 (2008).
McGregor, A., et al., "Trace reconstruction revisited," ESA 2014, 689-700 (2014).
Sok, L., et al., "Lattice based codes for insertion and deletion channels," IEEE Int. Symp. Inf. Theory vol. 2013, 684-688 (2013).
Duda, J. et al., "Fundamental bounds and approaches to sequence reconstruction from nanopore sequencers," preprint available at http://arXiv.org/abs/1601.02420 (2016).
Khorana, H. et al. "Syntheses of dideoxyribonucleotides," Journal of the American Chemical Society vol. 79, No. 4, pp. 1002-1003 (1957).
Letsinger, R. L. et al. "Oligonucleotide synthesis on a polymer support1,2," Journal of the American Chemical Society vol. 87, No. 15, pp. 3526-3527 (1965).
Letsinger, R. L. et al "Nucleotide chemistry. xiii. synthesis of oligothymidylates via phosphotriester intermediates," Journal of the American Chemical Society vol. 91, No. 12, pp. 3350-3355 (1969).
Letsinger, R. L. et al. "Synthesis of thymidine oligonucleotides by phosphite triester intermediates," Journal of the American Chemical Society vol. 98, No. 12, pp. 3655-3661 (1976).
Beaucage, S. et al. "Deoxynucleoside phosphoramiditesa new class of key intermediates for deoxypolynucleotide synthesis," Tetrahedron Letters vol. 22, No. 20, pp. 1859-1862 (1981).
Sinha, N. et al. "Polymer support oligonucleotide synthesis xviii1. 2): use of cyanoethyi-n, ndialkylamino-/n-morpholino phosphoramidite of deoxynucleosides for the synthesis of dna fragments simplifying deprotection and isolation of the final product," Nucleic Acids Research vol. 12, No. 11, pp. 4539-4557 (1984).
Fodor, S. P. et al. "Light-directed, spatially addressable parallel chemical synthesis," Science vol. 251 (1991).
Pease, A. C. et al. "Light-generated oligonucleotide arrays for rapid dna sequence analysis," Proceedings of the National Academy of Sciences vol. 91, No. 11, pp. 5022-5026 (1994).
Gao, X. et al. "In situ synthesis of oligonucleotide microarrays," Biopolymers vol. 73, No. 5, pp. 579-596 (2004).
Hughes, T. R. et al. "Expression profiling using microarrays fabricated by an ink-jet oligonucleotide synthesizer," Nature biotechnology vol. 19, No. 4, pp. 342-347 (2001).
Singh-Gasson, S. et al. "Maskless fabrication of light-directed oligonucleotide microarrays using a digital micromirror array," Nature biotechnology vol. 17, No. 10, pp. 974-978 (1999).
Nuwaysir, E. F. et al. "Gene expression analysis using oligonucleotide arrays produced by maskless photolithography," Genome research vol. 12, No. 11, pp. 1749-1755 (2002).
Ghindilis, A. L. et al. "Combimatrix oligonucleotide arrays: genotyping and gene expression assays employing electrochemical detection," Biosensors and Bioelectronics vol. 22, No. 9, pp. 1853-1860 (2007).
Kong, D. S. et al. "Parallel gene synthesis in a microfluidic device," Nucleic acids research vol. 35, No. 8, p. e61, (2007).

LeProust, E. M. et al. "Synthesis of high-quality libraries of long (150mer) oligonucleotides by a novel depurination controlled process," Nucleic acids research vol. 38, No. 8, pp. 2522-2540 (2010).
Au, L.-C. et al. "Gene synthesis by a Icr-based approach: High-level production of leptin-I54 using synthetic gene in*Escherichia coli*," Biochemical and biophysical research communications vol. 248, No. 1, pp. 200-203 (1998).
Stemmer, W. P. et al. "Single-step assembly of a gene and entire plasmid from large numbers of oligodeoxyribonucleotides," Gene vol. 164, No. 1, pp. 49-53 (1995).
Gibson, D. G. "Synthesis of dna fragments in yeast by one-step assembly of overlapping oligonucleotides," Nucleic acids research, p. gkp687 (2009).
Gibson, D. G. et al. "Chemical synthesis of the mouse mitochondrial genome," nature methods vol. 7, No. 11, pp. 901-903 (2010).
Tian, J. et al. "Accurate multiplex gene synthesis from programmable dna microchips," Nature vol. 432, No. 7020, pp. 1050-1054 (2004).
Borovkov, A. Y. et al. "Highquality gene assembly directly from unpurified mixtures of microarraysynthesized oligonucleotides," Nucleic acids research vol. 38, No. 19, pp. e180-e180 (2010).
Kosuri, S. et al. "Scalable gene synthesis by selective amplification of dna pools from high-fidelity microchips," Nature biotechnology vol. 28, No. 12, pp. 1295-1299 (2010).
Quan, J. et al. "Parallel on-chip gene synthesis and application to optimization of protein expression," Nature biotechnology vol. 29, No. 5, pp. 449-452 (2011).
Carr, P. A. et al. "Protein-mediated error correction for de novo dna synthesis," Nucleic acids research vol. 32, No. 20, pp. e162-e162 (2004).
Binkowski, B. F. et al. "Correcting errors in synthetic dna through consensus shuffling," Nucleic acids research vol. 33, No. 6, pp. e55-e55 (2005).
Wan, W. et al. "Error removal in microchip-synthesized dna using immobilized muts," Nucleic acids research, p. gku405 (2014).
Smith, J. et al. "Removal of polymerase-produced mutant sequences from per products," Proceedings of the National Academy of Sciences vol. 94, No. 13, pp. 6847-6850 (1997).
Fuhrmann, M. et al. "Removal of mismatched bases from synthetic genes by enzymatic mismatch cleavage," Nucleic acids research vol. 33, No. 6, pp. e58-e58 (2005).
Till, B. J. et al. "Mismatch cleavage by single-strand specific nucleases," Nucleic Acids Research vol. 32, No. 8, pp. 2632-2641 (2004).
Oleykowski, C. A. et al. "Mutation detection using a novel plant endonuclease," Nucleic acids research vol. 26, No. 20, pp. 4597-4602 (1998).
Saaem, I. et al. "Error correction of microchip synthesized genes using surveyor nuclease," Nucleic acids research, p. gkr887 (2011).
Dormitzer, P. R. et al. "Synthetic generation of influenza vaccine viruses for rapid response to pandemics," Science translational medicine vol. 5, No. 185, pp. 185ra68-185ra68 (2013).
Matzas, M. et al. "Highfidelity gene synthesis by retrieval of sequence-verified dna identified using high-throughput pyrosequencing," Nature biotechnology vol. 28, No. 12, pp. 1291-1294 (2010).
Lee, H. et al. "A high-throughput optomechanical retrieval method for sequence-verified clonal dna from the ngs platform," Nature communications vol. 6 (2015).
Kim, H. et al. "'shotgun dna synthesis' for the high-throughput construction of large dna molecules," Nucleic acids research, p. gks546 (2012).
Schwartz, J. J. et al. "Accurate gene synthesis with tag-directed retrieval of sequence-verified dna molecules," Nature methods vol. 9, No. 9, pp. 913-915 (2012).
Higuchi, R. et al. "A general method of in vitro preparation and specific mutagenesis of dna fragments: study of protein and dna interactions," Nucleic acids research vol. 16, No. 15, pp. 7351-7367 (1988).
Jansen, R. et al. "Identification of genes that are associated with dna repeats in prokaryotes," Molecular microbiology vol. 43, No. 6, pp. 1565-1575 (2002).

(56) References Cited

OTHER PUBLICATIONS

Sanger, F. et al. "DNA sequencing with chainterminating inhibitors," Proc. Natl. Acad. Sci. U.S.A. vol. 74, No. 12, pp. 5463-5467 (Dec. 1977).
Lander, E. S. et al. "Initial sequencing and analysis of the human genome," Nature vol. 409, No. 6822, pp. 860-921 (Feb. 2001).
Waterston, R. H. et al. "Initial sequencing and comparative analysis of the mouse genome," Nature vol. 420, No. 6915, pp. 520-562 (Dec. 2002).
Wheeler, D. A. et al. "The complete genome of an individual by massively parallel DNA sequencing," Nature vol. 452, No. 7189, pp. 872-876 (Apr. 2008).
Pevzner, P. A. et al. "An Eulerian path approach to DNA fragment assembly," Proc. Natl. Acad. Sci. U.S.A. vol. 98, No. 17, pp. 9748-9753 (Aug. 2001).
Zerbino, D. R. et al. "Velvet: algorithms for de novo short read assembly using de Bruijn graphs," Genome Res. vol. 18, No. 5, pp. 821-829 (May 2008).
Gnerre, S. et al. "High-quality draft assemblies of mammalian genomes from massively parallel sequence data," Proc. Natl. Acad. Sci. U.S.A. vol. 108, No. 4, pp. 1513-1518 (Jan. 2011).
Li, R. et al. "De novo assembly of human genomes with massively parallel short read sequencing," Genome Res. vol. 20, No. 2, pp. 265-272 (Feb. 2010).
Simpson, J. T. et al. "ABySS: a parallel assembler for short read sequence data," Genome Res. vol. 19, No. 6, pp. 1117-1123 (Jun. 2009).
Simpson, J. T. et al. "Efficient de novo assembly of large genomes using compressed data structures," Genome Res. vol. 22, No. 3, pp. 549-556 (Mar. 2012).
Kannan, S. et al. "More on reconstructing strings from random traces: insertions and deletions," Proc. IEEE Intl. Inform. Theory IEEE pp. 297-301. (2005).
Acharya, J. et al. "On reconstructing a string from its substring compositions," Proc. IEEE Intl. Symp. Inform. Theory IEEE pp. 1238-1242 (2010).
Tabatabaei Yazdi, S. M. H. et al. "A Rewritable, Random-Access DNA-Based Storage System" Sci. Rep. vol. 5, p. 14138 doi: 10.1038/srep14138 (Sep. 18, 2015).
Tabatabaei Yazdi, S. M. H. et al. Supplementary Information for "A Rewritable, Random-Access DNA-Based Storage System" Sci. Rep. vol. p. 5, 14138 (Sep. 18, 2015).
Tabatabaei Yazdi, S. M. H. et al. "Weakly Mutually Uncorrelated Codes" arXiv: 1601.08176; published to arxiv.org on Jan. 29, 2016.
Bancroft, C. et al. "Long-term storage of information in DNA," Science vol. 293, pp. 1763-1765 (2001).
Davis, J. "Microvenus" Art Journal vol. 55, pp. 70-74 (1996).
Church, G. M. et al. "Next-generation digital information storage in DNA," Science 337, 1628-1628 (2012).
Goldman, N. et al. "Towards practical, high-capacity, low-maintenance information storage in synthesized DNA," Nature vol. 494, pp. 77-80 (2013).
Grass, R. N. et al. "Robust chemical preservation of digital information on DNA in silica with error-correcting codes," Angewandte Chemie International Edition vol. 54, pp. 2552-2555 (Feb. 4, 2015).
Ross, M. G. et al. "Characterizing and measuring bias in sequence data," Genome Biol vol. 14, p. R51 (2013).
Cohen, G. D. et al. "Dc-constrained error-correcting codes with small running digital sum," Information Theory, IEEE Transactions on vol. 37, pp. 949-955 (1991).
Blaum, M. et al. "Error-correcting codes with bounded running digital sum," IEEE transactions on information theory vol. 39, pp. 216-227 (1993).
Gilbert, E. "Synchronization of binary messages," Information Theory, IRE Transactions on vol. 6, pp. 470-477 (1960).
Packer, H. "CRISPR and Cas9 for flexible genome editing," Technical report. (2014) Available at: www.idtdna.com/pages/products/genes/gblocks-gene-fragments/decoded-articles/decoded/2013/12/13/crispr-and-cas9-for-flexible-genome-editing (Accessed: Jan. 1, 2015).

Bryksin, A. V. et al. "Overlap extension PCR cloning: a simple and reliable way to create recombinant plasmids," Biotechniques vol. 48, p. 463 (2010).
Schuster, S. C. "Next-generation sequencing transforms today's biology," Nature methods vol. 5, pp. 16-18 (2008).
Morita, H. et al. "On the construction of maximal prefix-synchronized codes," Information Theory, IEEE Transactions on vol. 42, pp. 2158-2166 (1996).
Milenkovic, O. et al. "On the design of codes for DNA computing," In Coding and Cryptography, pp. 100-119 (Springer, 2006).
Rouillard, J.-M. et al. "Oligoarray 2.0: design of oligonucleotide probes for DNA microarrays using a thermodynamic approach," Nucleic acids research vol. 31, pp. 3057-3062 (2003).
Guibas, L. J. et al. "Maximal prefix-synchronized codes," SIAM Journal on Applied Mathematics vol. 35, pp. 401-418 (1978)
Massey, J. L. "Optimum frame synchronization," Communications, IEEE Transactions on vol. 20, pp. 115-119 (1972).
Chee, Y. M. et al. "Cross-bifix-free codes within a constant factor of optimality," Information Theory, IEEE Transactions on vol. 59, pp. 4668-4674 (2013).
Blackburn, S. R. "Non-overlapping codes," arXiv preprint arXiv:1303.1026 (2013).
Berman, P. et al. "Approximating maximum independent set in bounded degree graphs," In SODA vol. 94, pp. 365-371 (1994).
Gallager, R. G. "Low-density parity-check codes,Information Theory" IRE Transactions on vol. 8, No. 1, pp. 2128, (1962).
De Lind Van Wijngaarden, A. J. et al. "Frame synchronization using distributed sequences," Communications, IEEE Transactions on vol. 48, No. 12, pp. 2127-2138 (2000).
Bajic, D. et al. "Distributed sequences and search process," Communications, IEEE International Conference on vol. 1. IEEE, 2004, pp. 514-518 (2004).
Bilotta, S. et al. "A new approach to cross-bifix-free sets," IEEE Transactions on Information Theory vol. 6, No. 58, pp. 4058-4063 (2012).
Kiah, H. M. et al. "Codes for dna sequence profiles," IEEE Trans. Inf. Theory 62, 3125-46 (2016).
Tabatabaei Yazdi, S. M. H. et al. "DNA-Based Storage: Trends and Methods" arXiv:1507.01611 published to arxiv.org on Jul. 6, 2015.
Knuth, D. E. "Efficient balanced codes," Information Theory, IEEE Transactions on vol. 32, No. 1, pp. 51-53 (1986).
Gilbert, E. N. "A comparison of signalling alphabets," Bell System Technical Journal vol. 31, No. 3, pp. 504-522 (1952).
Graham, R. L. et al. "Lower bounds for constant weight codes," Information Theory, IEEE Transactions on vol. 26, No. 1, pp. 37-43 (1980).
Johnson, S. M. "A new upper bound for error-correcting codes," Information Theory, IRE Transactions on vol. 8, No. 3, pp. 203-207 (1962).
Tavares, S. "A study of synchronization techniques for binary cyclic codes," Ph.D. dissertation, Thesis (Ph. D.)—McGill University (1968).
gBlocks (TM) Gene Fragments Cloning Protocols http://www.idtdna.com/pages/docs/synthetic-biology/gblocks-user-guide.pdf (retrieved Nov. 15, 2016).
"Overlap Extension Polymerase Chain Reaction"—Wikipedia article https://en.wikipedia.org/wiki/Overlap_extension_polymerase_chain_reaction (retrieved Nov. 15, 2016).
Reed et al., I. S. "Polynomial codes over certain finite fields," Journal of the society for industrial and applied mathematics vol. 8, No. 2, pp. 300-304 (1960).
Kiah, H. M. et al. "Codes for dna storage channels," arXiv preprint arXiv:1410.8837, published to arxiv.org on Oct. 31, 2014.
Gabrys, R. et al. "Asymmetric lee distance codes for dna-based storage," arXiv preprint arXiv:1506.00740, published to arxiv.org on Jun. 2, 2015.
Kosuri, S. et al. "Large-scale de novo dna synthesis: technologies and applications," Nature methods vol. 11, No. 5, pp. 499-507 (2014).
Tian, J. et al. "Advancing high-throughput gene synthesis technology," Molecular BioSystems vol. 5, No. 7, pp. 714-722 (2009).

(56) References Cited

OTHER PUBLICATIONS

Ma, S. et al. "Dna synthesis, assembly and applications in synthetic biology," Current opinion in chemical biology vol. 16, No. 3, pp. 260-267 (2012).
Ma, S. et al. "Error correction in gene synthesis technology," Trends in biotechnology vol. 30, No. 3, pp. 147-154 (2012).
Michelson, A. et al. "Nucleotides part xxxii. synthesis of a dithymidine dinucleotide containing a 3': 5'-internucleotidic linkage," Journal of the Chemical Society (Resumed), pp. 2632-2638 (1955).
Hall, R. et al. "644. nucleotides. part xli. mixed anhydrides as intermediates in the synthesis of dinucleoside phosphates," Journal of the Chemical Society (Resumed), pp. 3291-3296 (1957).
Gilham, P. T. et al. "Studies on polynucleotides. i. a new and general method for the chemical synthesis of the c5 internucleotidic linkage. syntheses of deoxyribo-dinucleotides1," Journal of the American Chemical Society vol. 80, No. 23, pp. 6212-6222 (1958).
Roy, S. et al. "Synthesis of dna/rna and their analogs via phosphoramidite and h-phosphonate chemistries," Molecules vol. 18, No. 11, pp. 14 268-14 284 (2013).
Reese, C. B. "Oligo-and poly-nucleotides: 50 years of chemical synthesis," Organic & biomolecular chemistry vol. 3, No. 21, pp. 3851-3868 (2005).
Froehler, B. C. et al. "Synthesis of dna via deoxynudeoside h-phosphonate intermediates," Nucleic Acids Research vol. 14, No. 13, pp. 5399-5407 (1986).
Garegg, P. J. et al. "Nucleoside h-phosphonates. iii. chemical synthesis of oligodeoxyribonucleotides by the hydrogenphosphonate approach," Tetrahedron letters vol. 27, No. 34, pp. 4051-4054 (1986).
Acharya, J. et al. "Quadratic-backtracking algorithm for string reconstruction from substring compositions," Proc. IEEE Intl. Symp. Inform. Theory IEEE pp. 1296-1300 (2014).
Medvedev, P. et al. "Computability of models for sequence assembly," Algorithms in Bioinformatics; Springer pp. 289-301 (2007).
Compeau, P. E. et al. "How to apply de Bruijn graphs to genome assembly," Nature biotechnology vol. 29, No. 11, pp. 987-991 (2011).
Jacquet, P. et al. "Counting Markov types, balanced matrices, and Eulerian graphs," IEEE Trans. Inform. Theory vol. 58, No. 7, pp. 4261-4272 (2012).
Nakamura, K. et al. "Sequence-specific error profile of Illumina sequencers," Nucleic acids research p. gkr344, (2011).
Kløve, T. "Error correcting codes for the asymmetric channel," Department of Pure Mathematics, University of Bergen, (1981).
Ukkonen, E. "Approximate string-matching with q-grams and maximal matches," Theoretical computer science vol. 92, No. 1, pp. 191-211 (1992).
de Bruijn, N. G. "A combinatorial problem," *Koninklijke Nederlandse Akademie v. Wetenschappen* vol. 49, No. 49, pp. 758-764 (1946).
Ruskey, F. et al. "De Bruijn sequences for fixed-weight binary strings," SIAM Journal on Discrete Mathematics, vol. 26, No. 2, pp. 605-617 (2012).
Ahuja, R. K. et al. "Network flows: theory, algorithms, and applications," Prentice Hall (1993).
Stanley, R. P. "Enumerative combinatorics," Cambridge university press vol. 1. (2011).
Varshamov, R. "A class of codes for asymmetric channels and a problem from the additive theory of numbers," IEEE Trans. Inform. Theory vol. 19, No. 1, pp. 92-95 (1973).
Barvinok, A. I. "A polynomial time algorithm for counting integral points in polyhedra when the dimension is fixed," Mathematics of Operations Research vol. 19, No. 4, pp. 769-779 (1994).
Pevzner, P. A. et al. "Towards DNA sequencing chips," in Mathematical Foundations of Computer Science 1994. Springer, pp. 143-158 (1994).
Tan, S. et al. "Sets represented as the length-n factors of a word," in Combinatorics on Words Springer pp. 250-261 (2013).
Heinrich, K. "Path decompositions," Le Matematiche vol. 47, No. 2, pp. 241-258 (1993).

Cooper, J. N. et al. "Generalized de Bruijn cycles," Annals of Combinatorics vol. 8, No. 1, pp. 13-25 (2004).
Jiang, A. et al. "Rank modulation for flash memories," IEEE Trans. Inform. Theory vol. 55, No. 6, pp. 2659-2673 (2009).
Barg, A. et al. "Codes in permutations and error correction for rank modulation," IEEE Trans. Inform. Theory vol. 56, No. 7, pp. 3158-3165 (2010).
Farnoud, F. et al. "Error-correction in flash memories via codes in the Ulam metric," IEEE Trans. Inform. Theory vol. 59, No. 5, pp. 3003-3020 (2013).
Farnoud, F. et al. "Multipermutation codes in the Ulam metric for nonvolatile memories," Selected Areas in Communications IEEE Journal on vol. 32, No. 5, pp. 919-932 (2014).
Alderson, T. et al. "On maximum Lee distance codes," J. of Discrete Mathematics (2013).
Astola, J. "The Theory of Lee-codes," Lappeenranta University of Technology, Department of Physics and Mathematics, Research Report (Jan. 1982).
Delsarte, P. "An algebraic approach to the association schemes of coding theory," Doctoral dissertation, Universite Catholique de Louvain (1973).
Fazeli, A. et al. "Generalized Sphere Packing Bound," available at http://arxiv.org/abs/1401.6496 (2014).
Feng, J. et al. "Identification of Single Nucleotides in MoS2 Nanopores," arXiv preprint, arXiv:1505.01608 (2015).
Feynman, R. "There's Plenty of Room at the Bottom," Caltech, Pasadena Lecture (Dec. 29, 1959).
Hof, E. et al., "Capacity-achieving polar codes for arbitrarily permuted parallel channels," IEEE Trans. on Info. Theory vol. 59, No. 3, pp. 1505-1516 (Mar. 2013).
Kaykobad, M. "Positive solutions of positive linear systems," Lin. Alg. and its App. vol. 64, pp. 133-140 (Jan. 1985).
Kulkarni, A. A. et al. "Nonasymptotic upper bounds for deletion correcting codes," IEEE Trans. on Info. Theory vol. 59, No. 8, pp. 5115-5130 (Apr. 2013).
Mazumdar, A. et al. "Coding for high-density recording on a 1-D granular magnetic medium," IEEE Trans. on Info. Theory vol. 57, No. 11, pp. 7403-7417 (Jun. 2011).
Richardson, T. et al. "The capacity of low-density parity-check codes under message-passing decoding," IEEE Trans. on Info. Theory vol. 47, No. 2, pp. 599-618 (Aug. 2002).
Tal, I. et al. "Flow to construct polar codes," IEEE Trans. on Info. Theory vol. 59, No. 10, pp. 6562-6582 (Sep. 2013).
Bornholt, J. et al. "A dna-based archival storage system," Proceedings of the Twenty-First International Conference on Architectural Support for Programming Languages and Operating Systems ACM, pp. 637-649 (2016).
Brakensiek, J. et al. "Efficient low-redundancy codes for correcting multiple deletions," SODA vol. 27, pp. 1884-1892 (2016).
Brill, E. et al. "An improved error model for noisy channel spelling correction," Proceedings of the 38th Annual Meeting on Association for Computational Linguistics. Association for Computational Linguistics, pp. 286-293 (2000).
Cullina, D. et al. "An improvement to levenshtein's upper bound on the cardinality of deletion correcting codes," IEEE Transactions on Information Theory vol. 60, No. 7, pp. 3862-3870 (2014).
Damerau, F. J. "A technique for computer detection and correction of spelling errors," Commun. ACM vol. 7, No. 3, pp. 171-176 Available: http://doi.acm.org/10.1145/363958.363994 (Mar. 1964).
Gabrys, R. et al. "Graded bit-error-correcting codes with applications to flash memory," IEEE Transactions on Information Theory vol. 59, No. 4, pp. 2315-2327 (2013).
Helberg, A. S. et al. "On multiple insertion/deletion correcting codes," Information Theory, IEEE Transactions on vol. 48, No. 1, pp. 305-308 (2002).
Kumar, S. et al. "Mega3: integrated software for molecular evolutionary genetics analysis and sequence alignment," Briefings in bioinformatics vol. 5, No. 2, pp. 150-163 (2004).
Levenshtein, V. I. "Binary codes capable of correcting deletions, insertions, and reversals," in Soviet physics doklady vol. 10, No. 8, pp. 707-710 (1966).
Paluncic, F. et al. "A note on non-binary multiple insertion/deletion correcting codes," in IEEE Information Theory Workshop (2011).

(56) References Cited

OTHER PUBLICATIONS

Sala, F. et al. "Exact reconstruction from insertions in synchronization codes," arXiv preprint, arXiv:1604.03000 (2016).
Schoeny, C. et al. "Codes for correcting a burst of deletions or insertions," arXiv preprint, arXiv:1602.06820 (2016).
Schulman, L. J. "Asymptotically good codes correcting insertions, deletions, and transpositions," IEEE transactions on information theory vol. 45, No. 7, pp. 2552-2557 (1999).
Sloane, N. J. "On single-deletion-correcting codes," Codes and Designs, de Gruyter, Berlin, pp. 273-291 (2002).
Vilenchik, M. M. "Endogenous dna double-strand breaks: production, fidelity of repair, and induction of cancer," Proceedings of the National Academy of Sciences vol. 100, No. 22, pp. 12871-12876 (2003).
Wolf, J. "On codes derivable from the tensor product of check matrices," IEEE Transactions on Information Theory vol. 11, No. 2, pp. 281-284 (1965).
Adleman, L. M. "Molecular computation of solutions to combinatorial problems," Science vol. 266, pp. 1021-1024 (Nov. 1994).

\* cited by examiner

Example set of address primers that satisfy all three constraints and share a common concluding base

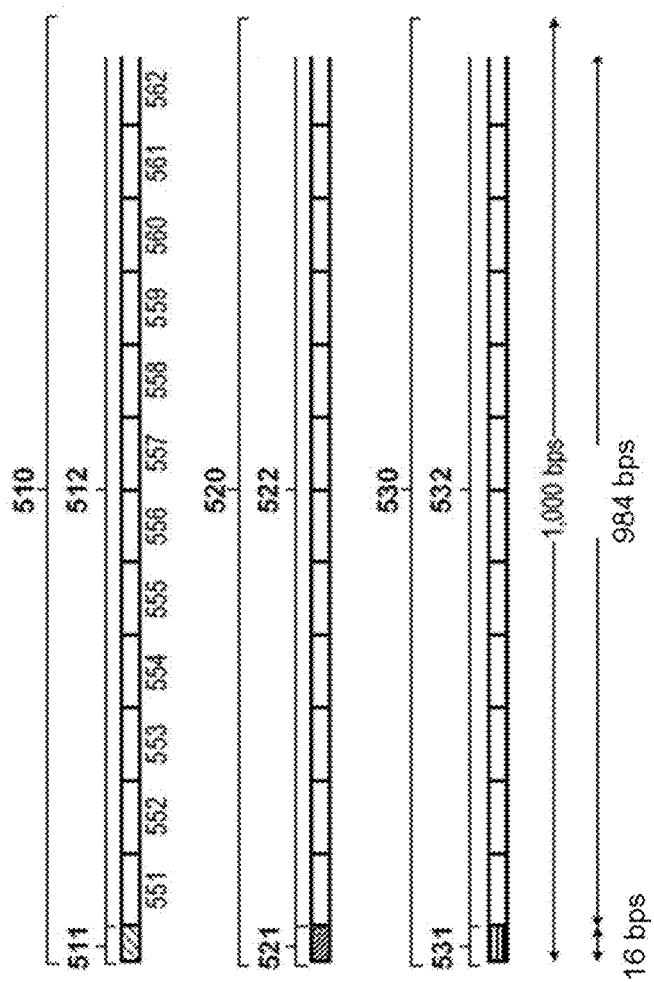

PORTABLE AND LOW-ERROR DNA-BASED DATA STORAGE

CROSS-REFERENCE TO RELATED APPLICATIONS

This application claims priority to U.S. provisional patent application No. 62/410,559, filed Oct. 20, 2016, which is hereby incorporated by reference in its entirety.

STATEMENT REGARDING FEDERALLY SPONSORED RESEARCH OR DEVELOPMENT

This invention was made with government support under 1618366 awarded by the National Science Foundation. The government has certain rights in the invention.

BACKGROUND

Modern data storage systems primarily rely on optical and magnetic media to record massive volumes of data that may be efficiently accessed, retrieved, and copied. As the amount of data created every day continues to increase, though, there is an ongoing need for reliable, high-density storage systems. Deoxyribonucleic acid (DNA) based storage platforms offer the possibility of achieving these goals. The proposed platforms have the potential to overcome existing bottlenecks of classical recorders as they offer ultrahigh storage densities on the order of $10^{15}$-$10^{20}$ bytes per gram of DNA. Experiments have shown that with DNA-based storage technologies one can record files as large as 200 MB, and ensure long-term data integrity through encapsulation and coding. In addition, one can accommodate random access and rewriting features through specialized addressing.

While DNA-based storage systems have been successfully demonstrated, such systems are limited. Current DNA-based storage architectures rely on synthesizing the DNA content once and retrieving it many times. Retrieval is exclusively performed via high-throughput sequencing technologies designed for laboratories that are not portable. Portable sequencers exclusively use nanopores, which have been known to introduce a prohibitively large number of deletion, insertion, and substitution errors (with some estimates as high as 38%) during read operations. Comparatively, the error rates of modern magnetic and optical systems rarely exceed 1 bit in 10 terabytes. Such high error rates have hindered the practical use of nanopore sequencers for DNA-based data storage applications.

SUMMARY

The embodiments herein provide methods, devices, and systems for low-error DNA-based data storage. Digital information is encoded in a plurality of nucleotide sequence blocks, each sequence block containing respective address sequences followed by data sequences. Each of the data sequences, identical as stored to that of a target nucleotide data sequence, contains a series of fixed-length substrings. Each fixed-length substring is 50% guanine and cytosine (G-C) and 50% adenine and thymine (A-T). The address sequences are designed to be highly suitable for random access (e.g., mutually uncorrelated and at a large Hamming distance from one another, among other properties). Thus, it is unlikely for one address to be confused with another. Further, the data sequence appearing after the address of each sequence block is encoded to avoid the appearance of any of the addresses, sufficiently long substrings of the addresses, or substrings similar to the addresses. To achieve this goal, prefix-synchronized encoding schemes are generalized to accommodate multiple sequence avoidance.

Once data is encoded in this fashion, the blocks may be read by a portable sequencer, e.g., a nanopore-based storage device, introducing deletion, insertion, and/or substitution errors into the nucleotide sequence blocks. To reduce the number of errors, one or more iterations of selection, alignment, and consensus procedures are performed on the sequence blocks read from the portable sequencer.

Particularly, a first example embodiment may involve reading the plurality of nucleotide sequence blocks from a nanopore-based storage device, introducing deletion, insertion, and/or substitution errors into the nucleotide sequence blocks. The embodiment includes selecting, by a computing device, a first group of the nucleotide sequence blocks read from the nanopore-based storage device, each having address sequences without any deletion, insertion, or substitution errors. The embodiment includes aligning, by the computing device, the data sequences from the first group of sequence blocks with one another, and performing, by the computing device, a first consensus procedure over the aligned nucleotides of the data sequences from the first group of sequence blocks, to produce a first output nucleotide data sequence.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

The features, objects and advantages other than those set forth above will become more readily apparent when consideration is given to the detailed description below. Such detailed description makes reference to the following drawings, wherein.

Figure 4A:
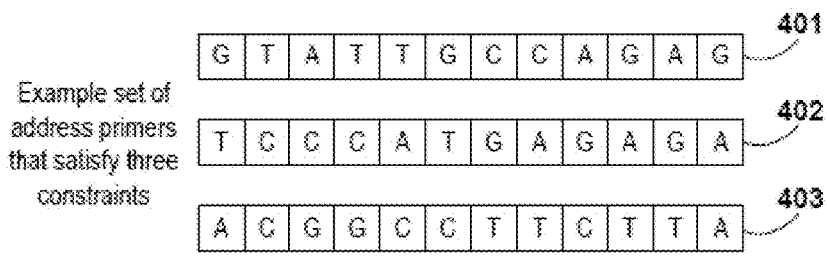
FIG. 4A illustrates a set of address primers that satisfy three constraints of address sequence design, according to example embodiments. Example address primer 401 corresponds to SEQ ID NO:01; Example address primer 402 corresponds to SEQ ID NO:02; and Example address primer 403 corresponds to SEQ ID NO:03.
Figure 4B:
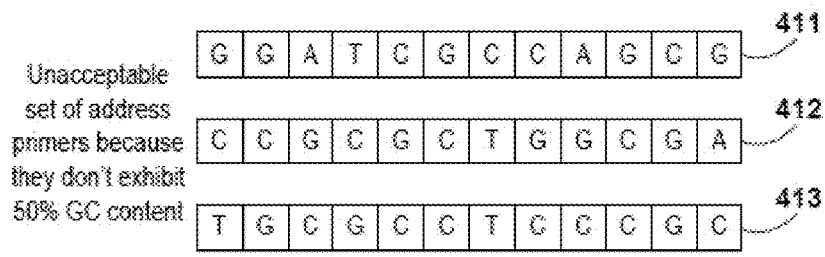
FIG. 4B illustrates a set of address primers that do not satisfy three constraints of address sequence design, according to example embodiments. Example address primer 411 corresponds to SEQ ID NO:04; Example address primer 412 corresponds to SEQ ID NO:05; and Example address primer 413 corresponds to SEQ ID NO:06.
Figure 4C:
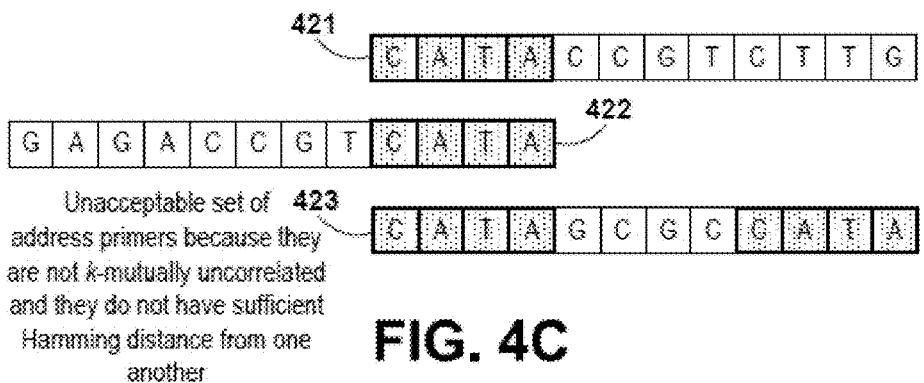
FIG. 4C illustrates a set of address primers that do not satisfy three constraints of address sequence design, according to example embodiments. Example address primer 421 corresponds to SEQ ID NO:07; Example address primer 422 corresponds to SEQ ID NO:08; and Example address primer 423 corresponds to SEQ ID NO:09.
Figure 4D:
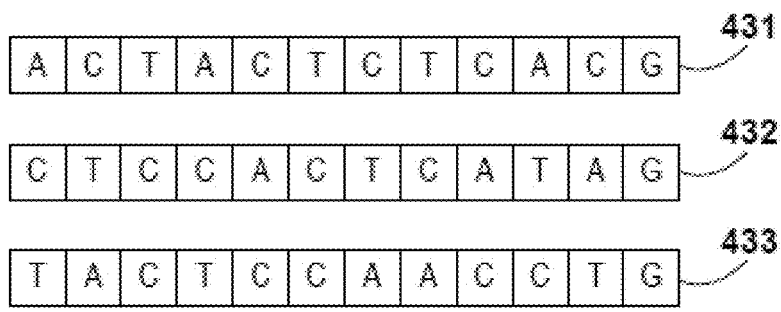

FIG. 4D illustrates a set of address primers that satisfy three constraints of address sequence design and also share a common concluding base, according to example embodiments. Example address primer 431 corresponds to SEQ ID NO:10; Example address primer 432 corresponds to SEQ ID NO:11; and Example address primer 433 corresponds to SEQ ID NO:12.

FIG. 5 illustrates multiple data blocks within a set of data blocks, according to example embodiments.

Figure 6:
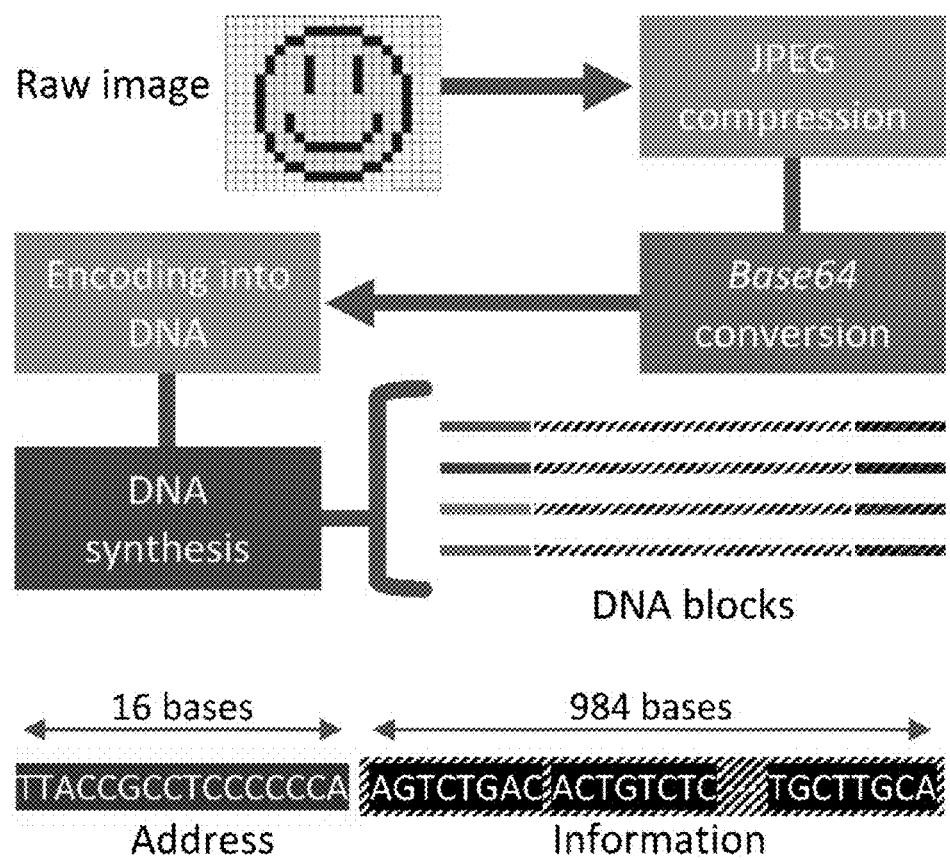

FIG. 6 depicts a flow chart illustrating a method, according to example embodiments.

Figure 7:
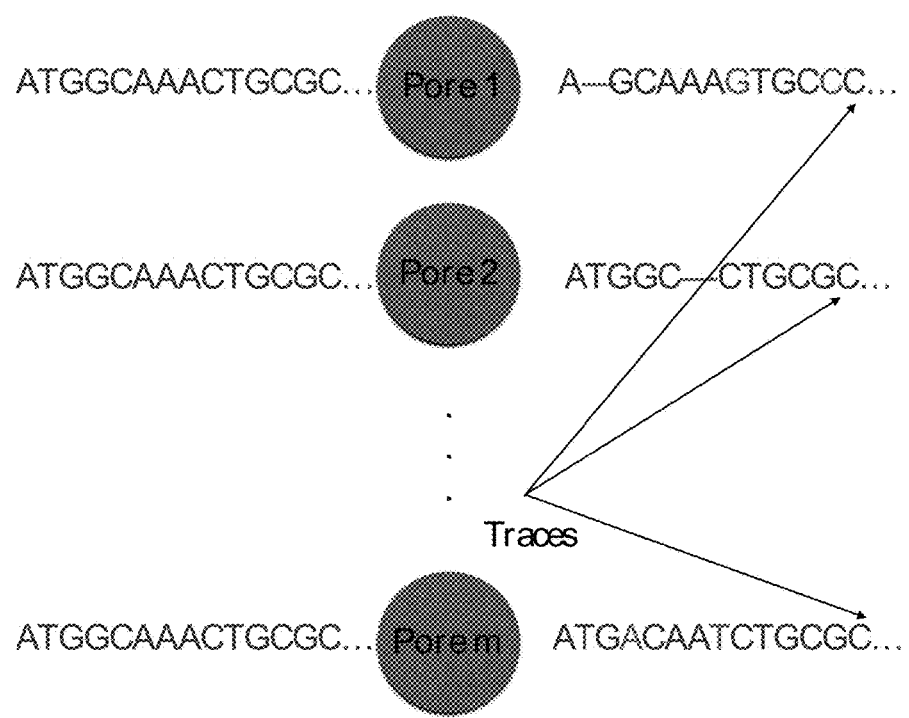

FIG. 7 depicts nanopore-based sequence estimation as a problem of sequence reconstruction from traces, according to example embodiments.

Figure 8:
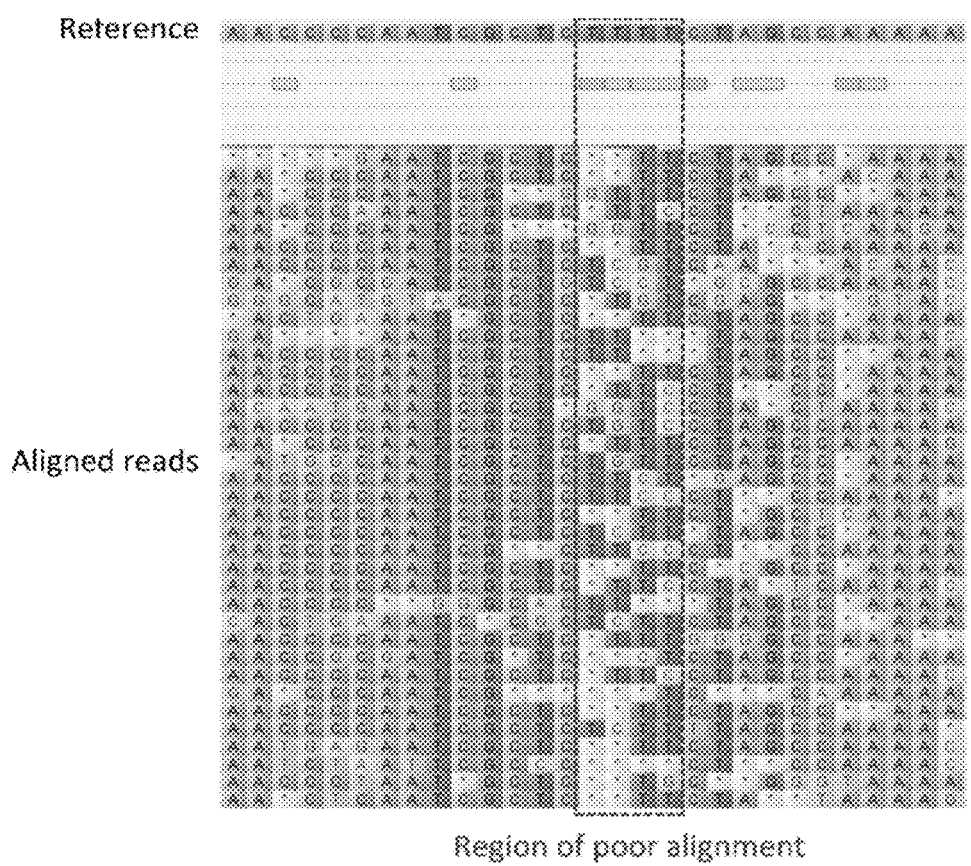

FIG. 8 is an example of an alignment iteration, according to example embodiments.

Figure 9:
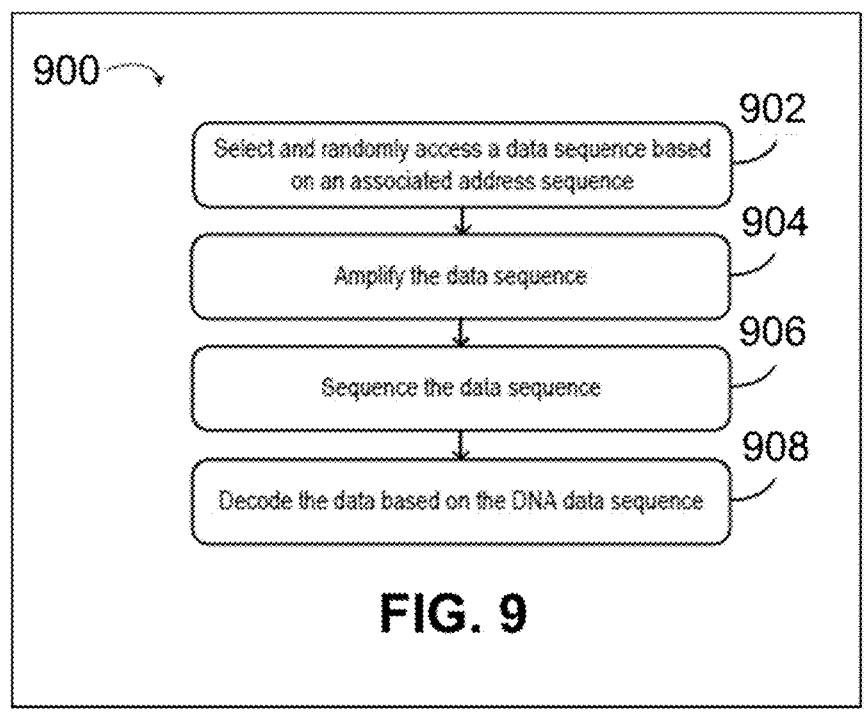

FIG. 9 depicts a flow chart illustrating a method, according to example embodiments.

Figure 10:
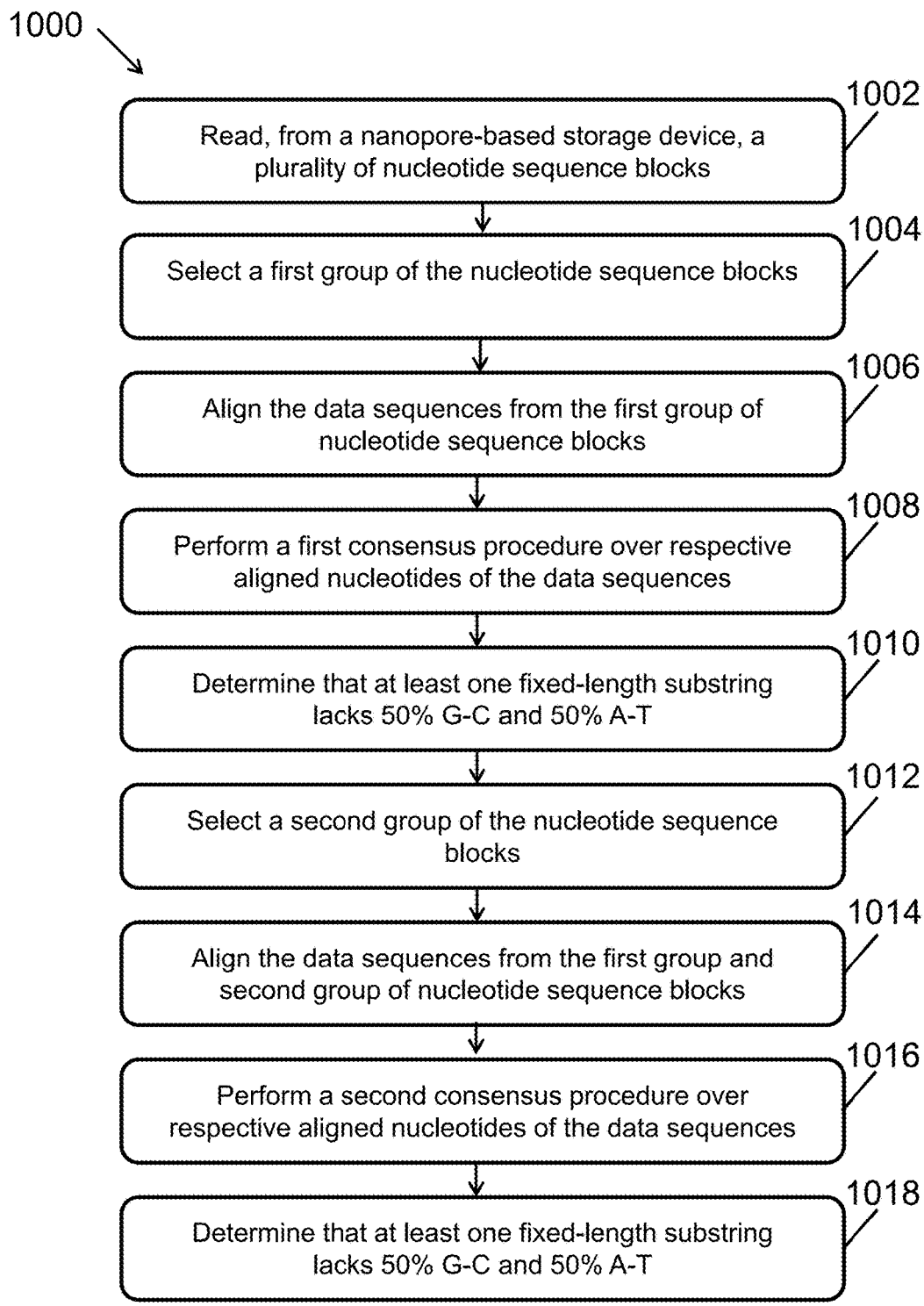

FIG. 10 depicts a flow chart illustrating a method, according to example embodiments.

Figure 11:
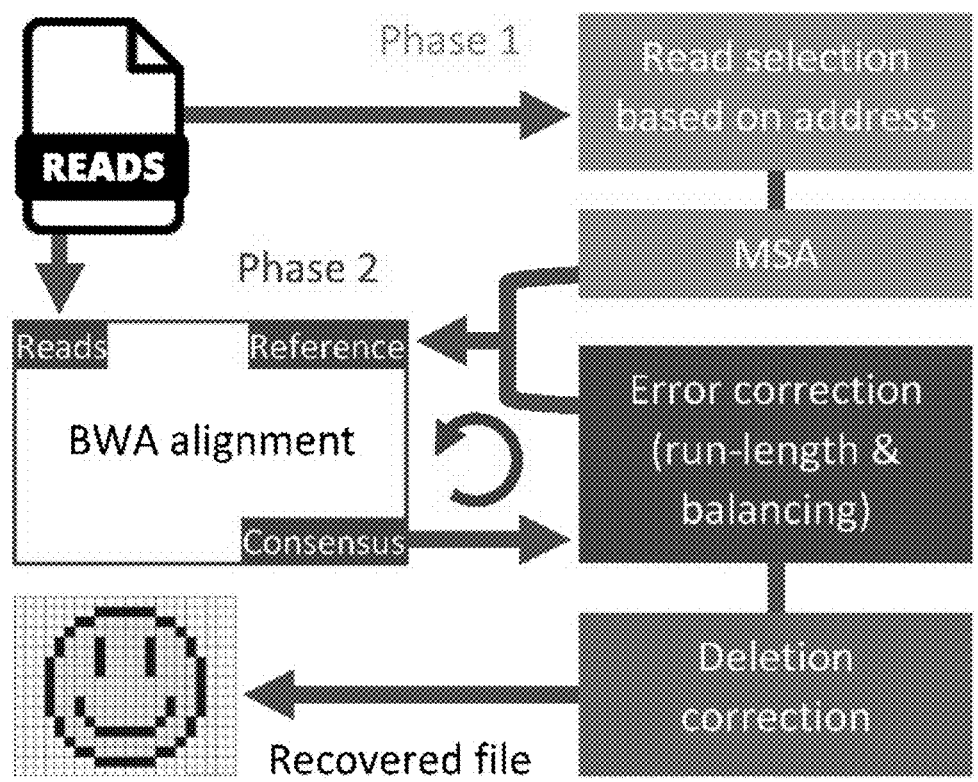

FIG. 11 depicts a flow chart illustrating a method, according to example embodiments.

Figure 12:
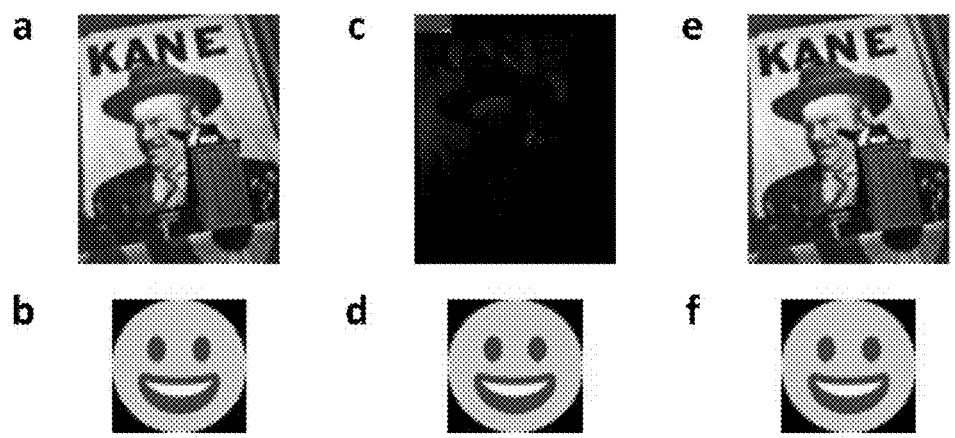

FIG. 12 depicts images at various stages of encoding, writing, and reading, according to example embodiments.

Figure 13:
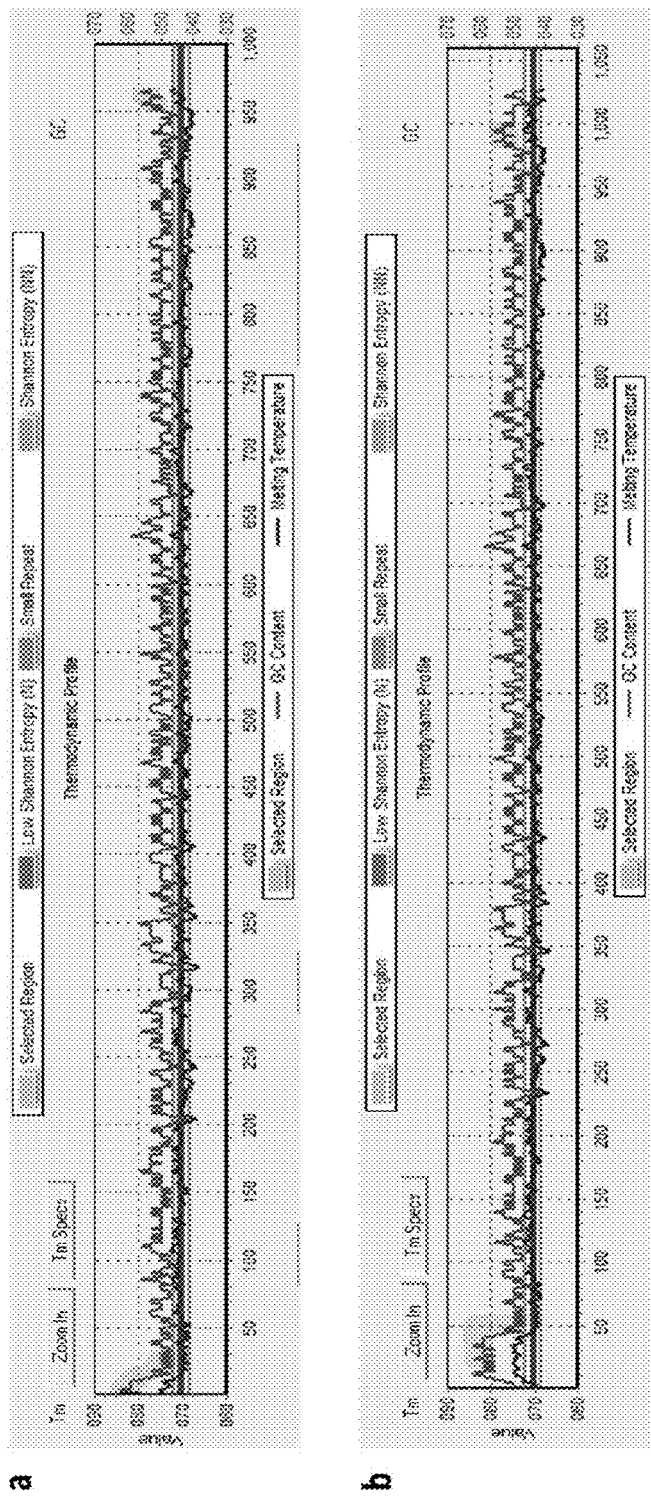

FIG. 13 depicts thermodynamic profiles of nucleotide sequence blocks having undesirable G-C content, according to example embodiments.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

Example methods, devices, media, and systems are described herein. Other embodiments can be utilized, and other changes can be made, without departing from the scope of the subject matter presented herein. Thus, these example embodiments are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

As used herein, the words "example" and "exemplary" mean "serving as an example, instance, or illustration." Any embodiment or feature described herein as being an "example" or "exemplary" is not necessarily to be construed as preferred or advantageous over other embodiments or features. The term "optimization" as used herein should not be interpreted to require that the "optimal" or "best" solution to any problem is found. Instead, "optimization" refers to a process through which better results may be obtained.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Regardless of how they may be implemented, the embodiments herein may make use of one or more computing devices. These computing devices may include, for example, client devices under the control of users, and server devices that directly or indirectly interact with the client devices. Such devices are described in the following section.

Example Computing Devices and Cloud-Based Computing Environments

Figure 1:
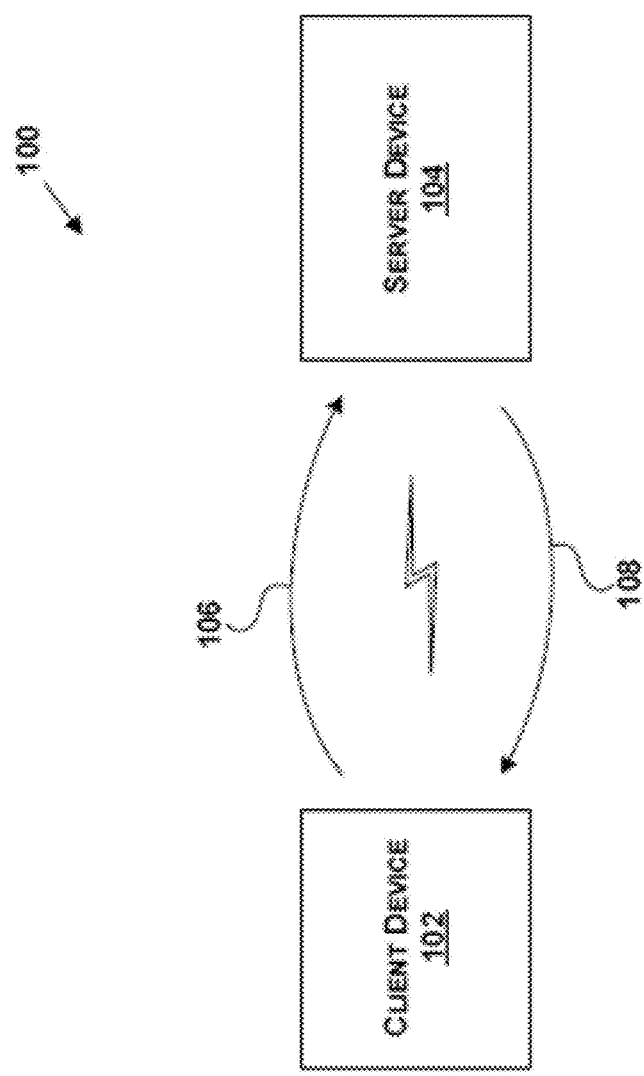
FIG. 1 is a high-level depiction of a client-server computing system, according to example embodiments.

FIG. 1 illustrates an example communication system 100 for carrying out one or more of the embodiments described herein. Communication system 100 may include computing devices. Herein, a "computing device" may refer to either a client device, a server device (e.g., a stand-alone server computer or networked cluster of server equipment), or some other type of computational platform.

Client device 102 may be any type of device including a personal computer, laptop computer, a wearable computing device, a wireless computing device, a head-mountable computing device, a mobile telephone, or tablet computing device, etc., that is configured to transmit data 106 to and/or receive data 108 from a server device 104 in accordance with the embodiments described herein. For example, in FIG. 1, client device 102 may communicate with server device 104 via one or more wireline or wireless interfaces. In some cases, client device 102 and server device 104 may communicate with one another via a local-area network. Alternatively, client device 102 and server device 104 may each reside within a different network, and may communicate via a wide-area network, such as the Internet.

Client device 102 may include a user interface, a communication interface, a main processor, and data storage (e.g., memory). The data storage may contain instructions executable by the main processor for carrying out one or more operations relating to the data sent to, or received from, server device 104. The user interface of client device 102 may include buttons, a touchscreen, a microphone, and/or any other elements for receiving inputs, as well as a speaker, one or more displays, and/or any other elements for communicating outputs.

Server device 104 may be any entity or computing device arranged to carry out the server operations described herein. Further, server device 104 may be configured to send data 108 to and/or receive data 106 from the client device 102.

Data 106 and data 108 may take various forms. For example, data 106 and 108 may represent packets transmitted by client device 102 or server device 104, respectively, as part of one or more communication sessions. Such a communication session may include packets transmitted on a signaling plane (e.g., session setup, management, and teardown messages), and/or packets transmitted on a media plane (e.g., text, graphics, audio, and/or video data).

Regardless of the exact architecture, the operations of client device 102, server device 104, as well as any other operation associated with the architecture of FIG. 1, can be carried out by one or more computing devices. These computing devices may be organized in a standalone fashion, in cloud-based (networked) computing environments, or in other arrangements.

Figure 2:
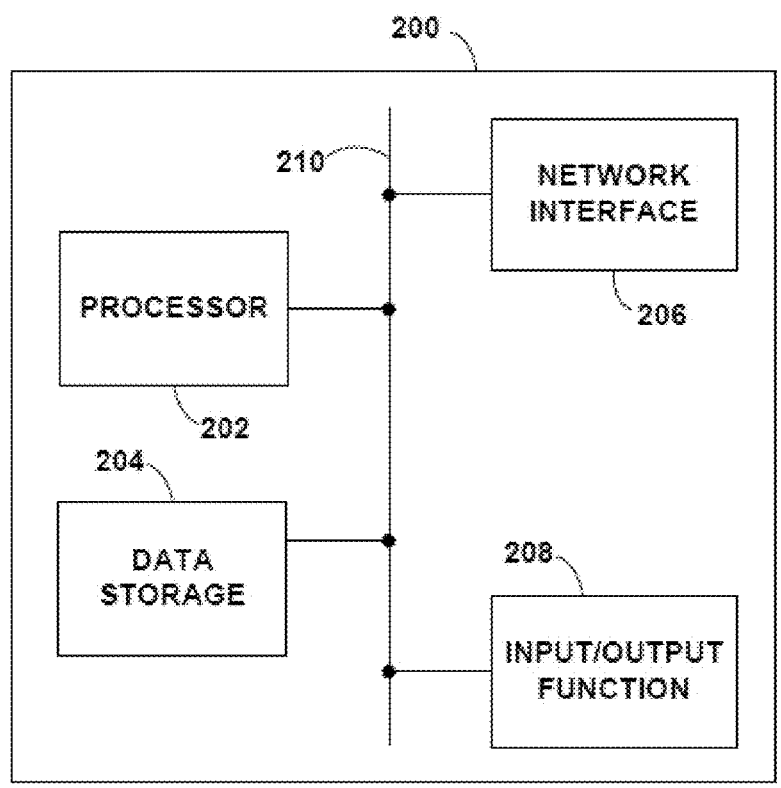
FIG. 2 illustrates a schematic drawing of a computing device, according to example embodiments.

FIG. 2 is a simplified block diagram exemplifying a computing device 200, illustrating some of the functional components that could be included in a computing device arranged to operate in accordance with the embodiments herein. Example computing device 200 could be a client device, a server device, or some other type of computational platform. For purpose of simplicity, this specification may equate computing device 200 to a server from time to time. Nonetheless, the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more CPUs, such as one or more general purpose processors and/or one or more dedicated processors (e.g., application specific integrated circuits (ASICs), digital signal processors (DSPs), network processors, etc.).

Data storage 204, in turn, may comprise volatile and/or non-volatile data storage and can be integrated in whole or in part with processor 202. Data storage 204 can hold program instructions, executable by processor 202, and data that may be manipulated by these instructions to carry out the various methods, processes, or operations described herein. Alternatively, these methods, processes, or operations can be defined by hardware, firmware, and/or any combination of hardware, firmware and software. By way of example, the data in data storage 204 may contain program instructions, perhaps stored on a non-transitory, computer-readable medium, executable by processor 202 to carry out any of the methods, processes, or operations disclosed in this specification or the accompanying drawings.

Network interface 206 may take the form of a wireline connection, such as an Ethernet, Token Ring, or T-carrier connection. Network interface 206 may also take the form of a wireless connection, such as IEEE 802.11 (Wifi), BLUETOOTH®, or a wide-area wireless connection. However, other forms of physical layer connections and other types of standard or proprietary communication protocols may be used over network interface 206. Furthermore, network interface 206 may comprise multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 3:
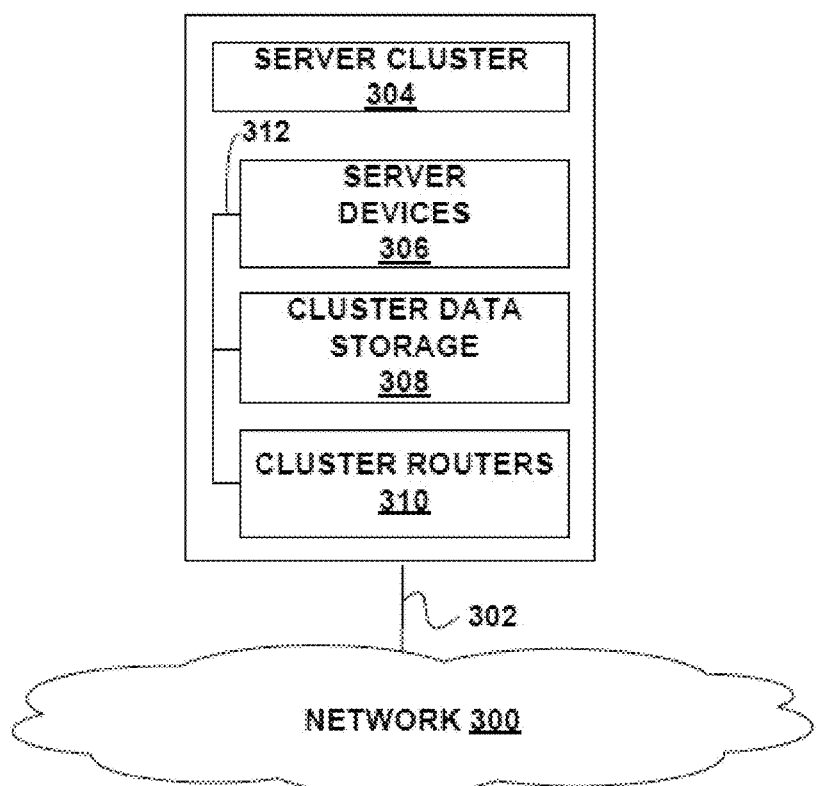
FIG. 3 illustrates a schematic drawing of a networked server cluster, according to example embodiments.

FIG. 3 depicts a cloud-based server cluster 304 in accordance with an example embodiment. In FIG. 3, functions of a server device, such as server device 104 (as exemplified by computing device 200) may be distributed between server devices 306, cluster data storage 308, and cluster routers 310, all of which may be connected by local cluster network 312. The number of server devices, cluster data storages, and cluster routers in server cluster 304 may depend on the computing task(s) and/or applications assigned to server cluster 304.

For example, server devices 306 can be configured to perform various computing tasks of computing device 200. Thus, computing tasks can be distributed among one or more of server devices 306. To the extent that these computing tasks can be performed in parallel, such a distribution of tasks may reduce the total time to complete these tasks and return a result. For purpose of simplicity, both server cluster 304 and individual server devices 306 may be referred to as "a server device." This nomenclature should be understood to imply that one or more distinct server devices, data storage devices, and cluster routers may be involved in server device operations.

Cluster data storage 308 may be data storage arrays that include disk array controllers configured to manage read and write access to groups of hard disk drives. The disk array controllers, alone or in conjunction with server devices 306, may also be configured to manage backup or redundant copies of the data stored in cluster data storage 308 to protect against disk drive failures or other types of failures that prevent one or more of server devices 306 from accessing units of cluster data storage 308.

Cluster routers 310 may include networking equipment configured to provide internal and external communications for the server clusters. For example, cluster routers 310 may include one or more packet-switching and/or routing devices configured to provide (i) network communications between server devices 306 and cluster data storage 308 via cluster network 312, and/or (ii) network communications between the server cluster 304 and other devices via communication link 302 to network 300.

Additionally, the configuration of cluster routers 310 can be based at least in part on the data communication requirements of server devices 306 and cluster data storage 308, the latency and throughput of the local cluster networks 312, the latency, throughput, and cost of communication link 302, and/or other factors that may contribute to the cost, speed, fault-tolerance, resiliency, efficiency and/or other design goals of the system architecture.

As a possible example, cluster data storage 308 may include any form of database, such as a structured query language (SQL) database. Various types of data structures may store the information in such a database, including but not limited to tables, arrays, lists, trees, and tuples. Furthermore, any databases in cluster data storage 308 may be monolithic or distributed across multiple physical devices.

Server devices 306 may be configured to transmit data to and receive data from cluster data storage 308. This transmission and retrieval may take the form of SQL queries or other types of database queries, and the output of such queries, respectively. Additional text, images, video, and/or audio may be included as well. Furthermore, server devices 306 may organize the received data into web page representations. Such a representation may take the form of a markup language, such as the hypertext markup language (HTML), the extensible markup language (XML), or some other standardized or proprietary format. Moreover, server devices 306 may have the capability of executing various types of computerized scripting languages, such as but not limited to Perl, Python, PHP Hypertext Preprocessor (PHP), Active Server Pages (ASP), JavaScript, and so on. Computer program code written in these languages may facilitate the providing of web pages to client devices, as well as client device interaction with the web pages.

Example DNA Structure and Sequencing

Genetic sequencing may involve determining the order of nucleotides in a biological sample, such as a block of DNA or RNA. Each nucleotide contains one base structure (or nucleobase) which may be adenine (A), guanine (G), cytosine (C), or thymine (T) for DNA. In RNA, thymine bases are replaced by uracil (U) bases. RNA can be divided into multiple categories, two of which are messenger RNA (mRNA) and micro RNA (miRNA). Messenger RNA includes RNA molecules that are transcribed from a DNA template and that convey genetic information from DNA to a ribosome, where they specify amino acid sequences. Micro RNA includes non-coding RNA molecules (usually containing about 17-25 nucleotides) and can regulate gene expression.

A strand of DNA or RNA may include tens, hundreds, thousands, millions, or billions of nucleotides in a particular ordering. Complete DNA sequences, or genomes, of various organisms have been discovered via a group of techniques generically referred to as "sequencing." Rather than attempting to sequence an entire genome in a monolithic operation, relatively short blocks of DNA or RNA (e.g., a few hundred or a few thousand nucleotides) may be sequenced individually. The sequencing of the individual blocks may involve steps of amplification and electrophoresis.

In order to sequence RNA, complementary DNA (cDNA) for single-strand RNA may be made, and the steps below may take place on the resultant DNA. However, other RNA sequencing techniques are possible, and the embodiments herein do not require the example sequencing technique below to be used.

Amplification refers to the copying of a block of DNA. Various amplification techniques may be used to make multiple copies of such a block from a small initial sample. For instance, polymerase chain reaction (PCR) is an amplification technique that can rapidly produce thousands of copies of a block.

Using PCR, the block containing the DNA sequencing target, primers (short single-stranded DNA fragments containing subsequences that are complimentary to the sequencing target), free nucleotides, and a polymerase are placed in a thermal cycler. Therein, the sequencing target undergoes one or more cycles of denaturation, annealing, and extension.

In the denaturation phase, the thermal cycler is set to a high temperature, which breaks the hydrogen bonds between bases of the sequencing target. The results are two complementary single-stranded DNA molecules. In the annealing phase, the thermal cycler is set to a lower temperature, which allows bonding of the primers to the single-stranded molecules. Once the primers are bonded to the appropriate locations of the single-stranded molecules, the extension phase begins. The thermal cycler is set to an intermediate temperature (e.g., a temperature between those used in the denaturation and annealing phases), and the polymerase binds complementary free nucleotides along the single-stranded molecules, effectively creating a copy of the original two-stranded DNA sequencing target.

These three phases repeat any number of times, creating an exponentially-growing number of copies of the original sequencing target. For example, in only a few hours, one million or more copies of the original sequencing target may be produced.

An initially popular method of DNA sequence was the Sanger sequencing method. In order to facilitate sequencing the original sequencing target by this method, dideoxynucleotides (ddNTPs) are added to the free nucleotides. A ddNTP has the same chemical structure as the free nucleotides, but is missing a hydroxyl group at the 3' position (e.g., at the end of the molecule to which DNA polymerase incorporates the subsequent nucleotide). Consequently, if a ddNTP is incorporated into a growing complementary strand during the extension phase, it may act as a polymerase inhibitor because the missing hydroxyl group prevents the strand from being elongated. Because the incorporation of ddNTPs is random, when the polymerization process iterates, DNA strands identical to the original sequencing target, but of different lengths, may be produced. If enough polymerization iterations take place for an original sequencing target of n base pairs, new copies of lengths 1 through n may be produced, each terminating with a ddNTP.

The DNA strands can be observed by radiolabeling the probe and resolving each of various lengths using electrophoresis. Alternatively, the ddNTPs for each types of base (e.g., A, C, G, and T) may be fluorescently-labeled with different dyes (colors) that emit light at different wavelengths. Thus, the A ddNTPs may have one color, the C ddNTPs may have another color, and so on. This enables the use of capillary electrophoresis to separate and detect the DNA strands based on size.

In electrophoresis, the replicated sequencing targets are placed in a conductive gel (e.g., polyacrylamide). The gel is subject to an electric field. For instance, a negatively-charged anode may be placed on one side of the gel and a positively-charged cathode may be placed on the other. Since DNA is negatively charged, the sequencing targets (i.e., the elongated strands) can be introduced to the gel near the anode, and they will migrate toward the cathode. Particularly, the shorter the sequencing target, the faster and further it will migrate. After some period of time, the sequencing targets may be arranged in order of decreasing length, with longer sequencing targets near the anode and shorter sequencing targets near the cathode. Similarly, fluorescently-labeled DNA strands by resolved and detected using capillary electrophoresis.

For fluorescently-labeled DNA strands, since the terminating nucleotide of each block is a colored ddNTP, computer imaging can be used to determine the sequence of nucleotides by scanning the colored ddNTP in each sequencing targets from those near the cathode to those near the anode. Alternatively, the colored ddNTP incorporated into each block can be identified as each block migrates past a fixed detector based on its size. By reading the ordered fluorescent molecules, the computer can provide a sequence of nucleotides represented as strings of bases in letter form (e.g., ACATGCATA).

Advances in computer processing and storage technologies have led to so-called "next-generation sequencing" techniques. While next-generation sequencing may include various procedures, in general they involve use of massively parallel computing to speed the sequencing process. For example, rather than processing sequenced DNA block one at a time, millions of such sequencing targets may be processed in parallel.

Most genetic sequencing techniques require equipment designed for laboratories, and are not portable. Portable sequencers rely on nanopore sequencing, which uses electrophoresis to transport an unknown DNA or RNA sample through a nanometer-scale pore. A constant electric field is applied across the nanopore surface, generating a current. The electric current will vary, characteristically, depending on the nucleotide composition of the unknown sample in the pore (e.g., A, T, C or G). By monitoring the electric current as the sample passes through the pore, a computer can provide a sequence of nucleotides represented as strings of bases in letter form.

Example Address Design

Herein below, the terms "address primers" and "address sequences" may be used interchangeably, and may be meant to represent similar concepts. Because an "address sequence" may be treated as a "primer" when selecting a corresponding data sequence during a reading process (e.g., when cutting DNA at a specific location to read the data that follows the primer), "address sequences" also represent "address primers."

In order to produce re-writable DNA-based digital storage that is randomly accessible, corresponding data may be assigned an address sequence. The address sequence may be selected from a set of address sequences. Further, the corresponding data may be encoded in a corresponding data sequence that does not conflict with the set of address sequences. As an example, an address sequence of length twenty may flank a corresponding data sequence (e.g., a corresponding data sequence of length 960) on a first side (e.g., the left side) of the corresponding data sequence.

The set of address sequences and corresponding data sequences may be designed using a two-step process. The first step may include designing address sequences of a given length that satisfy a set of constraints, making those address sequences suitable for selective random access. The first step may be semi-analytical, in that the first step may combine combinatorial methods with search techniques using a computing device. For example, the first step may select a set of possible address sequences based on combinatorics, and then perform a subsequent search of those possible address sequences to select a subset for use. In alternate embodiments, the first step may be purely analytical, in that the set of possible address sequences may be produced purely based on combinatorics.

The second step of designing address sequences and corresponding data sequences may involve encoding the information that is associated with the address sequences (i.e., address primers). The second step is described in a separate section of this description, while the first step is described below.

The set of constraints may avoid sequences that are prone to sequence errors. While the set of constraints might only be directly applied to address primer design, the set of constraints may also indirectly govern the information blocks (i.e., corresponding data sequences) associated with the address primers. In some embodiments, the following set of constraints may be imposed on the address sequences:

Constraint (1): The address sequences should have "constant GC content." If the sum of the number of guanines and cytosines within a DNA strand is equal, or nearly equal (e.g., within 1%, 5%, 10%, or 20% of 50%, or within 1-5 bases of 50%), to the sum of the number of adenines and thymines within the same DNA strand, that DNA stand has "constant GC content." DNA strands with 50% GC content are more stable than DNA strands with lower or higher GC content and have better coverage during sequencing. As described in a separate section, the corresponding data sequences may be encoded using prefix-synchronization. Thus, it may be beneficial to impose the "constant GC content" constraint on the address sequences (and their prefixes) so all fragments of encoded corresponding data sequences also have "constant GC content."

Example address primers 401, 402, 403 illustrated in FIG. 4A exhibit the quality of having "constant GC content." The sum of the number of guanine and cytosine bases in the example address primers 401, 402, 403 (i.e., six guanines or cytosines) is equivalent to the sum of the number of thymine and adenine bases in the example address primers 401, 402, 403 (i.e., six thymines or adenines). Therefore, the example address primers 401, 402, 403 have "constant GC content." This quality is also exhibited in candidate address primers 421, 422, 423 that are illustrated in FIG. 4C. However, the candidate address primers 411, 412, 413 illustrated in FIG. 4B do not have "constant GC content." As such, the candidate address primers 411, 412, 413 might not be selected as address primers. In some embodiments, the amount of GC content that satisfies "constant GC content" may be lessened for long address primes or for address primers with an odd number of bases.

Constraint (2): The address sequences may also have a large mutual Hamming distance (the Hamming distance is a measure of the number of positions at which two sequences of equal length are different from one another, i.e., the number of positions at which their corresponding symbols disagree). By using address sequences that have a large mutual Hamming distance, the probability of erroneous address selection may be reduced. An example choice for a minimum Hamming distance may be equal to half of the length of the address sequence. For example, if the address primers are twenty bases in length, ten bases may be a sufficient threshold Hamming distance. In alternate embodiments, other measures of similarity between address strings may be used (e.g., the Levenshtein distance).

Example address primers 401, 402, 403 illustrated in FIG. 4A satisfy the above mutual Hamming distance constraint. As illustrated, the Hamming distance between address primer 401 and address primer 402 is twelve, the Hamming distance between address primer 401 and address primer 403 is twelve, and the Hamming distance between address primer 402 and address primer 403 is eleven (all greater than half the length of the address primers, which is six).

Similarly, the candidate address primers 411, 412, 413 illustrated in FIG. 4B also exhibit sufficient mutual Hamming distance. As illustrated, the Hamming distance between candidate address primer 411 and candidate address primer 412 is twelve, the Hamming distance between candidate address primer 411 and candidate address primer 413 is nine, and the Hamming distance between candidate address primer 412 and candidate address primer 413 is eight (all greater than half the length of the address primers, which is six).

Conversely, the candidate address primers 421, 422, 423 illustrated in FIG. 4C do not exhibit sufficient mutual Hamming distance. As illustrated, the Hamming distance between candidate address primer 421 and candidate address primer 422 is four, the Hamming distance between candidate address primer 421 and candidate address primer 423 is four, and the Hamming distance between candidate address primer 422 and candidate address primer 423 is four (all less than half the length of the address primers, which is six). As such, the candidate address primers 421, 422, 423 might not be selected as address primers.

In some embodiments, bounded running digital sum (BRDS) codes may be used to satisfy constraint (1) and (2). The set of BRDS codes may then be modified or curated such that a subset of the BRDS codes satisfy constraint (3) described below.

Constraint (3): The set of address sequences may also be designed such that no address sequence has a prefix that appears as a suffix of the same or another address, and vice versa (i.e., the address sequences are "self-uncorrelated" and "mutually uncorrelated"). Because the address sequences may be used to provide unique identities for the corresponding data blocks (e.g., to permit random access), this constraint may ensure that their substrings do not appear in a "similar form" within other addresses. "Similarity", in this context, may refer to hybridization affinity, for example. In addition, this constraint may prevent long prefix-suffix matches from producing read assembly errors in blocks during concurrent information retrieval and sequencing.

In some embodiments, a minimum length of prefix may be defined, such that all prefixes equal to or longer than that length present within a set of address sequences do not appear as a suffix of the same or another address. Such a set of address sequences may be referred to as "weakly mutually uncorrelated." "Weakly mutually uncorrelated codes" differ from "mutually uncorrelated codes" in that "weakly mutually uncorrelated codes" allow short prefixes of codewords to also appear as suffixes of codewords. To more precisely describe a set of "weakly mutually uncorrelated" addresses, an integer, k, may be used. If $C \subseteq \mathbb{F}_q^n$ and $1 \le k \le n$, $C$ is a k-weakly mutually uncorrelated code if no proper prefix of length $\ell$, for all $\ell \ge k$, of a codeword in $C$ appears as a suffix of any other codeword, including itself.

This relaxation of prefix-suffix constraints associated with "weakly mutually uncorrelated" addresses may improve code rates and allow for increased precision DNA fragment assembly and selective addressing. Further, "weakly mutually uncorrelated" addresses may allow for an encoding of any form of data (e.g., images), as opposed to only text or numerals.

As illustrated in FIG. 4A, the example set of address primers 401, 402, 403 do not have any prefixes that appear as suffixes in the same or other addresses. As such, the example set of address primers 401, 402, 403 satisfy the third constraint. Further, the example set of address primers 401, 402, 403 satisfy constraints (1)-(3), and thus could be selected as a set of three address primers to use as address sequences.

Similarly, as illustrated in FIG. 4B, the candidate set of address primers 411, 412, 413 do not have any prefixes that appear as suffixes in the same or other addresses. As such, the candidate set of address primers 411, 412, 413 satisfy the third constraint. However, since the candidate set of address primers 411, 412, 413 only satisfies constraint (2) and constraint (3), the candidate set of address primers 411, 412, 413 might not be selected as a set of three address primers to use as address sequences.

Conversely, as illustrated in FIG. 4C, the candidate set of address primers 421, 422, 423 do have prefixes of length four (CATA) which appear as suffixes in the same or other addresses and vice versa. As such, the candidate set of address primers 421, 422, 423 do not satisfy the third constraint. Because the candidate set of address primers 421, 422, 423 only satisfies constraint (1), the candidate set of address primers 421, 422, 423 may not be selected as a set of three address primers to use as address sequences.

The example address sequences 401, 402, 403 illustrated in FIG. 4A are provided to illustrate a set of three address sequences that satisfy constraints (1), (2), and (3). In some embodiments, though, additional constraints may be imposed on the set of address sequences. For example, in some embodiments, the address sequences selected for use may all share a common base (e.g., guanine) as the last base in each sequence. Further, the address sequences selected for use may only use the three remaining bases (e.g., adenine, cytosine, and thymine), excluding the common base, to define the remainder of the address sequences. Such a set of example address sequences 431, 432, 433, which satisfy both constraints (1)-(3), as well as the common base constraint, is illustrated in FIG. 4D.

The set of address sequences should satisfy all three of the above constraints in order to be used. In some embodiments, additional constraints may be imposed, such as a lack of secondary folding characteristics for the corresponding DNA structures to avoid folding that would cause errors in PCR amplification and fragment rewriting. The lack of secondary structure at room temperature may be verified by the mfold and/or Vienna packages, for instance. An example of five address sequences that not only satisfy constraints (1)-(3), but also do not exhibit secondary folding characteristics is the following:

```
CGTAGTCAGCGTGTCAATCA       (SEQ ID NO: 14)

TGCACAGTCGAGCTATCACA       (SEQ ID NO: 15)

GACTGACTGATGACGACTGA       (SEQ ID NO: 16)

GCTATATGCGAGTCGAGTCA       (SEQ ID NO: 17)

GTACACTCAGCATCGACTCA       (SEQ ID NO: 18)
```

The above construction of address sequences may be analogous to a largest independent set problem. For example, the problem could be analogously defined as follows:

For a given length n and minimum Hamming distance d, let V denote the set of address sequences of length n that satisfy the following conditions:
Elements of V are GC-balanced
Elements of V avoid secondary structure
Construct a simple graph G(V,E), with vertices V and edges E, where (u, v)∈E, for u, v∈V, if one of the following conditions holds:
The Hamming distance between u and v is less than d
u and v are correlated, i.e., u and v share a proper prefix and suffix
Thus, it is verifiable that a set of strings A⊆V is an independent set in G if and only if A is a set address sequence that satisfies all four of the above conditions. Hence, the problem of finding the largest independent set in G may be equivalent to finding the largest set of address sequences of length n that satisfy the above conditions. Such a problem may be an NP-hard problem.

Constructing address sequences that simultaneously satisfy constraints (1) to (3) and determining bounds on the largest number of such sequences may take a significant amount of resources. Thus, a semi-constructive address designing process in which balanced error-correcting codes are designed independently, and subsequently expurgated so as to identify a large set of mutually uncorrelated sequences, may be used. This may be referred to as a "greedy approach for address construction." For example, the process may begin by selecting a single self-uncorrelated, GC-balanced DNA sequence (e.g., AATTACTAAGCGACCTTCTC; SEQ ID NO:19). Thereafter new address sequences may be added, one at a time, such that the total set of added sequences still satisfies constraints (1)-(3).

Each new address may be added by searching GC-balanced DNA sequences of the same length as the current set of address sequences (e.g., 20 bases) that have a minimum Hamming distance of at least half the length of the current set of addresses (e.g., 10). The first address sequence that is self-uncorrelated and mutually uncorrelated with the current address set may then be added to the address set. Secondary structure of the address sequences may also be taken into account in the "greedy approach for address construction," in some embodiments.

In alternate embodiments, a purely analytical method can be used to generate a complete set of address sequences. For given integers n and k≤n, let m=n−k+1 and let a, b, and c be the binary component words. Then, $C \in \{A, T, C, G\}^n$ can be constructed according to the following steps:

(1) Encode a using a binary block code $C \subseteq \{0,1\}^{k-1}$ of length k−1, and minimum Hamming distance d. Let $\Phi_1$ denote the encoding function, so that $\Phi_1(a) \in C_1$.

(2) Generate a mutually uncorrelated code $C_2 \subseteq \{0,1\}^m$ of length m, dimension s, and minimum Hamming distance d. This may be done by fixing two positive integers, t and $\ell$, such that $m=t(\ell-1)$. For each codeword $\in C_2$, b can be mapped to a word of length $n=(t+1)\ell+1$ given by:

$$a = 0^t b_1^{\ell-1} b_l^{2(\ell-1)} 1 \ldots b_{(t-1)(\ell-1)+1}^{t(\ell-1)} 1$$

Using the mutually uncorrelated code $C_2$, encode b. Let $\Phi_2$ denote the encoding function, so that $\Phi_2(b) \in C_2$.

(3) Generate a codeword c from a balanced code $C_3$ of length n, minimum Hamming distance d and of size A (n, d, n/2). Let $\Phi_3$ denote the underlying encoding function, so that $\Phi_3(c) \in C_3$.

The output of the above encoder is $\Psi(\Phi_1(a), \Phi_2(b), \Phi_3(c))$, where $\Psi(a, b): \{0,1\}^s \times \{0,1\}^s \rightarrow \{A, T, C, G\}^s$ is an encoding function that maps the pair a, b to a DNA string $c=(c_1, \ldots, c_s) \in \{A, T, C, G\}^s$, according to the following rules:

$$\text{for } 1 \leq i \leq s, c_i \begin{cases} A & \text{if } (a_i, b_i) = (0, 0) \\ C & \text{if } (a_i, b_i) = (0, 1) \\ T & \text{if } (a_i, b_i) = (1, 0) \\ G & \text{if } (a_i, b_i) = (1, 1) \end{cases}$$

Example Data Encoding

During a data storage process, once the address sequences are designed, various embodiments may include generating and selecting codeword blocks, also referred to herein as "nucleotide sequence blocks," to encode the data sequence following the address sequence. The codeword blocks may be selected to avoid replicating any of the address sequences, sufficiently long substrings of the address sequences, and substrings similar to the address sequences. This may be done to enable random access of the data by read processes described herein. For example, such a selection of codeword blocks may prevent DNA blocks that correspond to stored data from being accidentally accessed, amplified, or selected by a primer that is designed to access a specific address sequence (i.e., the primer may cut the DNA sequence nonspecifically at multiple regions if the address sequences were not independent from the codeword blocks, which could lead to reading errors or an inadvertent destruction of data).

An example "low-error" codeword block, c, of length N is represented by a row vector ab over the four-symbol alphabet $\mathcal{D} = \{A, C, G, T\}$, assuming the following:

If $a=(a_1, \ldots, a_n)$ and $b=(b_1, \ldots, b_m)$ are two vectors over the same alphabet $\mathcal{D}$, then ab is the vector obtained by appending b to a, i.e., $ab=(a_1, \ldots, a_n, b_1, \ldots, b_m)$.

If $a=(a_1, \ldots, a_n)$, then $a_i^j=(a_i, \ldots, a_j)$ is used to denote the substring of a starting at position i and ending at position j, $1 \leq i \leq j \leq n$.

If $a=(a_1, \ldots, a_n)$, then $a^{(i)}=a_i^n a_1^{i-1}$ is the cyclic shift of the vector a starting at position $1 \leq i \leq n$. Note that for the shift to be well defined the initial condition $a^{(1)}=a$ is imposed.

Each "low-error" block c starts with a unique address sequence of length p base pairs; the remaining codewords in the block comprise the data sequence (i.e., the encoded information). Accordingly, c=ab, where a denotes the address and b denotes the data sequence. For a set $\mathcal{A}$ of all allowed address sequences of length p and a set $\mathcal{B}$ of all valid data sequences of length N−p, $a \in \mathcal{A}$ and $b \in \mathcal{B}$.

"Low-error" codeword blocks have the first property that for any two (not necessarily distinct) addresses a, $a' \in \mathcal{A}$ and for any data sequence $b \in \mathcal{B}$, $a' \neq (ab)_i^{p+i-1}$ for $i \geq 2$, i.e., a' may not appear as a substring in $a_2^p b$.

An example methodology to produce such "low-error" blocks having this first property is as follows. For a binary set (code) $C \subseteq \{0,1\}^n$, $C^{cyclic}$ denotes the set of all cyclic shifts of elements in $C$, that is, if $a \in C$ then $a^{(k)} \in C^{cyclic}$, for $1 \leq k \leq n$. For two binary codes $C_1, C_2 \in \{0,1\}^n$ such that $C_1^{cyclic} \cap C_2 = \emptyset$, if $a \in C_1$, then $a^{(i)} \notin C_1, C_2$ for $2 \leq i \leq n$.

For binary codes $C_1, C_2$, the set of addresses $\mathcal{A} \subseteq \{A, C, G, T\}^{2n}$ may be constructed accordingly:

$$\mathcal{A} = \{\psi(f,g) | f \in C_1, g \in C_3\}. \quad (1)$$

The address length is p=2n, and $C_3$ is a binary code of length p=2n. The properties of $C_3$ may be chosen so as to enforce a minimum Hamming distance on the addresses, and $\psi(\cdot,\cdot)$ is a bijection that maps two binary strings into one codeword. More precisely, if $f=(f_1, \ldots, f_m) \in \{0,1\}^m$ and $g=(g_1, \ldots, g_m) \in \{0,1\}^m$, then $\psi(f, g)=h \in \{A, C, G, T\}^m$, where $h=(h_1, \ldots, h_m)$ is obtained according to the rules:

$$h_i = \begin{cases} A, & \text{if } (f_i, g_i) = (0, 0) \\ T, & \text{if } (f_i, g_i) = (0, 1) \\ C, & \text{if } (f_i, g_i) = (1, 0) \\ G, & \text{if } (f_i, g_i) = (1, 1) \end{cases}, \text{ for } 1 \leq i \leq m. \quad (2)$$

The set of data sequences $\mathcal{B}$ is defined as a collection of nucleotide sequences of the form $$\mathcal{B} = \{s_1 \ldots s_m | \text{for } m \geq 1, s_i \in \mathcal{S}\}, \quad (3)$$

where $$\mathcal{S} = \{\psi(f,g) | f \in C_2, g \in C_4\}. \quad (4)$$

The properties of $C_2, C_4$, binary codes of length n, may be tuned to accommodate balancing and Hamming distance constraints.

The sequences in $\mathcal{A}$ and $\mathcal{B}$, prepared as in (1) and (3) above, satisfy the first "low-error" property:

Consider two arbitrary address sequences a, a'∈A and a data sequence b∈B. For simplicity of notation assume that $a=\psi(f,g)$, $a'=\psi(f',g')$ and that $b=s_1 \ldots s_n$, where $s_i=\psi(f_i,g_i)$ for $1 \leq i \leq m$. Since the mapping $\psi(\cdot,\cdot)$ defined is one-to-one, the claimed result will follow if it can be proven that ff' does not appear as a substring anywhere in $f_2^n ff_1 \ldots f_m$. This can be done by checking two conditions:

f' does not appear as a substring anywhere in $f_2^n f$. Otherwise, f' would have to be a proper cyclic shift of f, i.e., there would exist an index $2 \leq i \leq n$ such that $f'=f^{(i)}$. But then $f'=f^{(i)} \notin C_1$, which contradicts the assumption that f, f'∈$C_1$.

ff' does not appear as a substring in ff$_1$ ... f$_m$. Otherwise, there would exist a sequence f$_i$ for 1≤i≤m that appears as a substring in f'f'. This would in turn imply that f$_i$ is a cyclic shift of f', i.e., f$_i \in C_1^{cyclic}$. This contradicts the initial assumptions that f$_i \in C_2$ and $C_1^{cyclic} \cap C_2 = \emptyset$.

"Low-error" codeword blocks have the second property that the address sequences of $A$ are as distinguishable as possible. One example methodology to produce such "low-error" blocks having this second property is to select address sequences having a large edit distance, that is, the smallest number of deletions, insertions, and substitutions necessary to convert one sequence of $A$ into another. Another example methodology to produce such "low-error" blocks having this second property is to maximize the Hamming distance between pairs of different address sequences, as described above with respect to address design. When mutually uncorrelated addresses with a large Hamming distance are selected, codewords that avoid one of the addresses in the set $A$ may inherently avoid all other addresses in the set.

Finally, "low-error" codeword blocks have the third property that the data sequences of $B$ each have a locally balanced G-C content. One example methodology to produce such "low-error" blocks having this third property is to select data sequences containing a series of fixed-length substrings, each substring having 50% G-C and 50% A-T. Locally balanced G-C content may reduce synthesis errors when writing codeword blocks, eliminate some secondary structures formed by codeword blocks, and aid in correction of deletion errors introduced from reading sequence blocks from a nanopore-based storage device (described below).

Example Random Access Writing

The example embodiment of FIG. 5 illustrates multiple data blocks 510, 520, 530 within a set of data blocks. The data blocks 510, 520, 530 may each include address sequences 511, 521, 531 of length sixteen base pairs flanking corresponding data sequences 512, 522, 532 (e.g., corresponding data sequences of length 984 base pairs) on a first side (e.g., the left side) of the corresponding data sequences 512, 522, 532. As illustrated by different patterns in FIG. 5, the address sequences on either side of the data blocks (e.g. address sequence 511 and 513) represent unique, different addresses. The address sequences 511, 521, 531 of the corresponding data sequences 512, 522, 532 may provide specificity of access. The corresponding data sequences 512, 522, 532 may be made up of individual substrings 551-562 that are each eight base pairs in length, for example.

As illustrated in the example embodiment of FIG. 5, the data blocks 510, 520, 530 may be 1,000 base pairs in length. In alternate embodiments, other lengths of data blocks, address sequences, corresponding data sequences, and/or number of corresponding data sequences may be used. Codeword blocks shorter than 1,000 base pairs, for example, may be less expensive to synthesize, but may also incur an increased storage overhead, due to coverage redundancy or addressing. The inverse may be true for codeword blocks longer than 1,000 base pairs.

The process described above could be used to encode large files. To accommodate large file sizes at low synthesis cost, the data is first compressed. Decompression may cause catastrophic error propagation if mismatches are introduced in the DNA strings either during synthesis or sequencing. Even one single substitution error in the compressed domain may render the file unrecognizable.

As an example, the process described above could be used to encode and write two images files: A poster for the movie Citizen Kane (released in 1941), and a color Smiley Face emoji. The total size of the images was 10,894 bytes. The two images were compressed into a JPEG format and then converted into a binary string using Base64 (Base64 allows one to embed images into HTML files). The resulting size for the two compressed images was 3,633 bytes. The compressed files were written to codeword block lengths of 1,000 base pairs (bp).

For a codeword block length of 1,000 bp, sets of 123×14=1,722 consecutive bits were grouped in the compressed file and translated into data sequences comprising 123×8=984 bases. The G-C content of each substring of 8 bases was then balanced via specialized constrained coding techniques, similar to those described above for address design. See FIG. 6.

For a substring length of n=8, addresses of length p=2n=16 were selected. $C_2$ and $C_4$ were selected to be the set of all balanced binary words (i.e., words with half 0s and half 1s) and all binary words of length 8, respectively. Note that $\equiv C_2 \equiv (_4^8)$, $|C_4|=2^8$. In addition, according to the defining relation (4), above, ψ(f, g) is a G-C-balanced DNA string if and only if f is a balanced binary word. Accordingly, because $C_2$ is a balanced set, $S$ is simply the set of all G-C-balanced DNA substrings of length 8 bp. The cardinality of the latter set is $|S|=(_4^8) \times 2^8$, and $B$ is formed by stringing together elements from $S$. Importantly, balancing the G-C-content of each substring of a given length limits the longest homopolymer (i.e., a repeating nucleotide) length to the same value—in this case, 8.

To construct an address set $A$, $C_1 = \{10000000, 01111111\}$ and $C_3$ was selected to be the set of all binary strings of length 16. Here, the number of addresses is $|A|=2^{17}$. Alternatively, the code $C_3$ may be selected to have large Hamming distance, which would result in the same Hamming distance for the constructed addresses (here, an extended [16,11,4] BCH code was used for $C_3$). It is easy to verify that in this case $A$ and $B$ satisfy the condition of property (1), above. Also of importance are the numerically computed Hamming distances between the chosen addresses of the blocks and all the substrings of the encoded DNA blocks of the same length. For each address of length 16, the distance between the address and all the substrings in the codewords was recorded. Then, the "most similar" substrings for the address sequences in terms of the Hamming distance were identified and replaced if necessary to achieve larger discriminative power during PCR reactions.

The block addresses are listed in Table 1, along with the average and minimum Hamming distances between the chosen addresses and encoded substrings. Note that the choice of the BCH code $C_3$ is justified by the fact that the minimum Hamming distance between a DNA address and any encoded information substring equals $d_H$=4.

TABLE 1

Block addresses and Hamming distance profiles of the addresses vs DNA blocks.

| Block (length) | Average Hamming distance | Minimum Hamming distance | Forward address | SEQ ID NO |
|---|---|---|---|---|
| 1 (1,000 bp) | 8.75 | 4 | TATGCGCGACCCCCCT | 20 |
| 2 (1,000 bp) | 8.62 | 4 | CCGAATATCAAAAATC | 21 |
| 3 (1,000 bp) | 9.27 | 5 | AATCCGCGACCCCCGA | 22 |
| 4 (1,000 bp) | 9.28 | 5 | CCCAATATCAAAATAG | 23 |
| 5 (1,000 bp) | 9.28 | 5 | AAACCGCGACCCCGCT | 24 |
| 6 (1,000 bp) | 9.34 | 5 | GCCTATATCAAAATTC | 25 |
| 7 (1,000 bp) | 9.30 | 6 | TAAGCGCGACCCCGGA | 26 |
| 8 (1,000 bp) | 9.33 | 5 | CGCAATATCAAATAAC | 27 |
| 9 (1,000 bp) | 9.33 | 5 | ATACCGCGACCCGCCA | 28 |

TABLE 1-continued

Block addresses and Hamming distance
profiles of the addresses vs DNA blocks.

| Block (length) | Average Hamming distance | Minimum Hamming distance | Forward address | SEQ ID NO |
|---|---|---|---|---|
| 10 (1,000 bp) | 9.32 | 5 | GGCTATATCAAATATG | 29 |
| 11 (1,000 bp) | 9.27 | 5 | TTAGCGCGACCCGCGT | 30 |
| 12 (1,000 bp) | 9.29 | 5 | GGGTATATCAAATTAC | 31 |
| 13 (1,000 bp) | 9.35 | 4 | TTTGCGCGACCCGGCA | 32 |
| 14 (1,000 bp) | 9.2 | 5 | CGGAATATCAAATTTG | 33 |
| 15 (1,000 bp) | 9.2 | 5 | ATTCCGCGACCCGGGT | 34 |
| 16 (1,000 bp) | 9.01 | 5 | AAAGCCCCTGCGCCGT | 35 |
| 17 (880 bp) | 9.23 | 5 | TTACCGCCTCCCCCCA | 36 |

DNA Synthesis

Once encoded, DNA codeword blocks are synthesized. In an example, blocks are synthesized as DNA blocks. Despite a large amount of work on oligo-based data storage, DNA blocks were used as they have many advantages over oligo sequences, including:

- Long DNA sequences may be easily assembled with minimal or no coverage redundancy even when one uses no addressing schemes. When using addresses, one effectively mitigates the need for assembly if the address sequences are carefully designed.
- Long DNA sequences offer largest coding efficiency as the address overhead for oligos may be as large as 20%, while for DNA blocks it amounts to a mere 2%. Furthermore, all known coding schemes offer best performance for long block lengths.
- Most third generation sequencing technologies are being developed to accommodate long reads, and hence long read sequencers will become the dominant market product in the near future; at the same time, a number of companies offer smallest costs per base pair for long DNA sequences.

In one example, the image-encoded codeword blocks described above were synthesized. Before performing the actual writing process, the synthesis complexity of each DNA codeword was tested by special-purpose software. Synthesis errors are highly correlated with the total repeat density (direct, inverse and palindromic repeat elements), extreme variations in GC-content, and secondary structures, especially if such properties hold near the 3' and 5' termini of the sequence.

Although all the 17 DNA blocks passed the initial complexity test, one of the blocks was not synthesizable due to high GC-content in one address sequence. To overcome the problem, the address was redesigned, and the sequences were augmented by adapters. The sequences augmented by adapters passed all subsequent tests without issues. A small subset of adapters which have been optimized to be compatible with the DNA block synthesis process are available. These adapters can be appended to the 5' and 3' ends of any sequence and may increase synthesis feasibility whenever complex secondary structures are encountered.

Example Random Access Reading

Sequence Reconstruction from Traces

The problem of reconstructing a sequence from a number of reads that were generated by passing the sequence through (independent) nanopores requires using specialized bioinformatics tools. The main challenge is the identification of the pores of a nanopore-based storage device that produce poor-quality readouts, and perform accurate sequence estimation based on high-quality reads only.

Variants of the problem have been studied as sequence reconstruction via traces (See FIG. 7). The general traces problem may be stated as follows: Reconstruct a string x of length n from a set of m subsequences generated by randomly editing symbols in x with a given probability fixed for all subsequences. By focusing on edits of the form of deletions, which occur with a small constant probability, m=poly(n) traces suffice for exact reconstruction. Here, poly(n) stands for a polynomial expression in n. This result has been improved to show that for certain alphabet sizes, even a sub-polynomial number of traces suffices. Several algorithms for high probability, error-free reconstruction have been described. The reconstruction problem for the case in which the traces represent nanopore DNA reads has also been considered. A noiseless setup in which each read has some fixed length and a noisy setup in which reads were subjected to substitution errors has also been considered. Finally, a different type of noise model that more realistically captures the properties of nanopore sequencing technologies has been studied. In particular, bounds on the parameter m necessary for reliable reconstruction were given for the case in which edits change the homopolymer lengths. Accurate sequence reconstructing via new profile coding techniques has been proposed. None of these models, considerations, and proposals, however, can be applied directly to reading a nucleotide sequence block from a nanopore-based storage device, because the pores introduce a complex mixture of errors that are not necessarily confined to homopolymer changes. Additionally, the noise parameters of different pores may differ significantly, and would be dependent on the particular sequence structure.

Data Sequence Reads

Given different read qualities, it is important to first identify reads with small fractions of deletion and insertion errors which will be used in the first step of reconstruction. For this purpose, pilot sequences may be utilized. In one example, a pilot sequence is used to assess the performance of a noisy channel, because it is known both to the transmitter and receiver. The transmitter sends the pilot sequence to the receiver which can, based on the knowledge of the sequence, estimate the probability of error. If the error probability is small, the transmitter asks for the information sequence to be transmitted; otherwise, the transmitter delays transmission. Because the addresses of nucleotide sequence blocks are known to the user, they may serve as pilot sequences. More precisely, based on the quality of the address sequence, a specific read may be selected for, or excluded from, reconstruction. Once desired reads are identified, the reads are aligned, and a consensus procedure involving majority voting at each sequence coordinate or for each homopolymer may be performed. This procedure may be performed iteratively, to correct consensus errors (See FIG. 8).

Once encoded/written, the data sequences may later be read for data retrieval. As described above, the data sequences, based on their associated address sequences, may be randomly accessed for reading. An example method 900 of performing the random access reading is illustrated in FIG. 9.

At block 902, the method 900 may include selecting the specific data sequence, based on its associated address sequence, from the "soup" of DNA that contains all the address sequences and corresponding data sequences (here, a DNA "soup" refers to an unordered mixture of DNA). Because the associated address sequence is unique among other address sequences and subsections of other data sequences within the "soup", due to the way in which it was generated, such a selection of the address sequence is also unique. The selection may be made using a primer which cuts a strand of DNA in the soup at the location of the address sequence. Even given a relatively extremely low likelihood of error in selecting the correct address sequence (e.g., between 1 in $10^{15}$ or 1 in $10^{16}$), the selection (i.e., block 902) may be performed multiple times (e.g., three times). The selection may be performed multiple times so that in later blocks a majority rule can be applied, which may serve as a way of eliminating potential mistaken readings through repetition (i.e., multiple data sequences may be compared against one another for consistency). Block 902 may include selecting one or more address sequences and an associated data sequence, together comprising a data block.

At block 904, the data sequence, or a data block which includes both the relevant address sequence(s) and the corresponding data sequence, may be amplified. Block 904 may be performed using PCR, for example. PCR may amplify the address sequence(s) and the corresponding data sequence at a rapid rate (e.g., between $2^{30}$ and $2^{40}$ times amplification per hour). Similarly, if multiple selections were made (e.g., if three address sequence selections were made in block 902), block 904 may be repeated multiple times, one for each data sequence.

At block 906, the method 900 may include DNA sequencing the data sequence. This may include reading the data sequence from a nanopore-based storage device, for example. As with prior blocks, if multiple selections and amplifications were made (e.g., if three address sequence selections were made in block 902 and three data sequence amplifications were made in block 904), block 906 may be repeated multiple times, one for each data sequence.

During the reading process, the data sequence being read may be selected from the "soup" and analyzed. In doing so, that respective data sequence may be removed from the "soup" and/or destroyed. As such, the reading process may include a replenishment of the read data sequence. The replenishment may include return a copy of the amplified/DNA sequenced data sequence to the "soup."

Low-Error Sequencing

In some embodiments, reading sequence blocks introduces one or more of deletion, insertion, and substitution errors into the sequence blocks. In one example, reads from portable, nanopore-based sequencers have sequence-dependent substitution, deletion, and insertion errors. In such embodiments, post-sequencing processing may be performed to reduce or eliminate substitution, deletion, and insertion errors.

In some embodiments, the low-error sequencing enables portable readout of synthetic nucleotide sequences. In some embodiments, the low-error sequence includes reading, from a nanopore-based storage device, a plurality of nucleotide sequence blocks. In some embodiments, each of the nucleotide sequence blocks as stored in the nanopore-based storage device contains respective address sequences followed by data sequences. In some embodiments, each of the data sequences as stored is identical to that of a target nucleotide data sequence. In some embodiments, each of the data sequences contains a series of fixed-length substrings and each of the fixed-length substrings is 50% guanine and cytosine and 50% adenine and thymine. In some embodiments, reading introduces deletion, insertion, or substitution errors into the nucleotide sequence blocks. In some embodiments, the low-error sequencing includes selecting, by a computing device, a first group of the nucleotide sequence blocks read from the nanopore-based storage device, each having address sequences without any deletion, insertion, or substitution errors. In some embodiments, the low-error sequencing includes aligning, by the computing device, the data sequences from the first group of nucleotide sequence blocks with one another, and performing, by the computing device, a first consensus procedure over respective aligned nucleotides of the data sequences from the first group of nucleotide sequence blocks. In some embodiments, the first consensus procedure produces a first output nucleotide data sequence.

In some embodiments, the first output nucleotide data sequence matches the target nucleotide data sequence.

In some embodiments, the low-error sequencing includes determining that at least one fixed-length substring of the first output nucleotide data sequence is not 50% guanine and cytosine and 50% adenine and thymine. In some embodiments, the low-error sequencing includes, in response to determining that at least one fixed-length substring of the first output nucleotide data sequence is not 50% guanine and cytosine and 50% adenine and thymine, selecting a second group of the nucleotide sequence blocks read from the nanopore-based storage device, each having address sequences with exactly one deletion, insertion, or substitution error, and performing a second consensus procedure over respective aligned nucleotides of the data sequences from the first group of nucleotide sequence blocks, wherein the second consensus procedure produces a second output nucleotide data sequence.

In some embodiments, the second output nucleotide data sequence matches the target nucleotide data sequence.

In some embodiments, each of the fixed-length substrings consists of 8 nucleotides. In some embodiments, each of the fixed-length substrings contains run length values for runs of one or more consecutive nucleotides therein. In some embodiments, the consensus procedure determines deletion, insertion, or substitution errors in the fixed-length substrings of the data sequences based on inconsistencies between a number of consecutive nucleotides and an associated run length value.

In some embodiments, each of the address sequences is 8-32 nucleotides in length. In some embodiments, each of the data sequences is 512-2048 nucleotides in length.

In some embodiments, each of the address sequences is p nucleotides in length. In some embodiments, a particular address sequence of the address sequences does not appear as a non-address substring in any of the nucleotide sequence blocks. In some embodiments, each of the address sequences is a Hamming distance of at least p/2 from one another.

In some embodiments, each of the address sequences is 50% guanine and cytosine and 50% adenine and thymine.

An example method 1000 of performing low-error sequencing (e.g., as block 906 of example method 900) is illustrated in FIG. 10.

At block 1002, the method 1000 may include reading a plurality of nucleotide sequence blocks, each containing a respective address sequence followed by a data sequence. The plurality of nucleotide sequence blocks may be stored in, and read from, a nanopore-based storage device. The data sequences as stored may be identical to that of a target nucleotide data sequence, each containing a series of fixed-length substrings. The fixed-length substrings may be 50% G-C and 50% A-T. Reading the plurality of nucleotide sequence blocks may introduce deletion, insertion, or substitution errors into the nucleotide sequence blocks.

At block 1004, the method 1000 may include selecting a first group of the nucleotide sequence blocks read from the nanopore-based storage device, the blocks of the first group each having an address sequence without any deletion, insertion, or substitution errors. The means for selecting may be a computing device.

At block 1006, the method 1000 may include aligning the data sequences from the first group of nucleotide sequence blocks with one another. The means for aligning may be a computing device. The computing device may perform a multiple sequence alignment, using MSA algorithms such as Kalign, Clustal Omega, Coffee, MUSCLE, MAFFT, BWA, MATLAB®, etc. The computing device may further align a preliminary consensus sequence with the data sequences from the first group of nucleotide sequence blocks. The computing device may determine the preliminary consensus sequence through the alignment itself. Alternatively, the computing device may utilize a preliminary consensus sequence determined through other means. For example, the preliminary consensus sequence may be a "majority homopolymer" of a set of two or more consensus sequences determined with different MSA algorithms. In an example, the "majority homopolymer" of three preliminary consensus sequences AAATTGCC (e.g., obtained through Kalign), AATTTGCA (e.g., obtained through Clustal Omega), and AAATTGC (e.g., obtained through MUSCLE) is AAATTGCA, because two sequences contain a homopolymer of three As at the first position, two sequences contain a homopolymer of two Ts in the positions to follow; and all three sequences contain G and C. A is included in the last position of the consensus.

Parameters for a specific MSA algorithm may be selected to maximize alignment performance for sequences read from nanopore-based storage devices. In one example, parameters for MSA algorithms may be those provided in Table 2, below.

lowing the address sequence (e.g., from the left), may select for each segment a majority homopolymer length. The computing device may further determine whether, for a majority homopolymer length, each fixed-length substring of the data sequence has 50% G-C and 50% A-T, and if not, select a non-majority homopolymer length instead. The computing device may further determine whether, for a majority homopolymer length, the total length of the data sequence is evenly divisible by the length of the fixed-length substring, and if not, select a non-majority homopolymer length instead.

In one example of blocks 1006 and 1008 of the method 1000, a preliminary consensus sequence ($C_p$) of a first group of three nucleotide sequence blocks, each having address sequences without any deletion, insertion, or substitution errors (reads 1-3) is first determined. The data sequences of each block are shown below:

(SEQ ID NO: 41)
$C_p$   TTCACCCAAAAACCCGAAAACCGCTTCAGCGA (SEQ ID NO: 42)
read1   TTCACCCCAAAACCGAAAACCGCTTCACGA (SEQ ID NO: 43)
read2   TTCACCCAAAAACCCGAAAACCGCTTCAGCGA (SEQ ID NO: 44)
read3   TTCACCCAAAAACCCGAAAACCGCTTCAGCGA A MATLAB® MSA algorithm is then performed, producing the following result:

| Ca | TT | C | A | CCCC | AAAA* | CCC | G | AAAA | CC | G | C | TT | C | A | * | C | G | A |
|---|---|---|---|---|---|---|---|---|---|---|---|---|---|---|---|---|---|---|
| read1 | TT | C | A | CCC* | AAAA* | CC* | G | AAAA | CC | G | C | TT | C | A | * | C | G | A |
| read2 | TT | C | A | CCCC | AAAA* | CCC | G | AAAA | CC | G | C | TT | C | A | G | C | G | A |
| read3 | TT | C | A | CCC* | AAAAA | CCC | G | AAAA | CC | G | C | TT | C | A | G | C | G | A |
|  | $r_1$ | $r_2$ | $r_3$ | $r_4$ | $r_5$ | $r_6$ | $r_7$ | $r_8$ | $r_9$ | $r_{10}$ | $r_{11}$ | $r_{12}$ | $r_{13}$ | $r_{14}$ | $r_{15}$ | $r_{16}$ | $r_{17}$ | $r_{18}$ |

TABLE 2

Parameter choices for MSA algorithms. The parameters are selected to offer the best empirical performance for nanopore read alignments.

| Algorithm | Parameters |
|---|---|
| Kalign | Gap open penalty = {5, 11}, Gap extension penalty = {0.2, 0.85}, Terminal Gap Penalties = {0.1, 0.45}, Bonus Score = {5.2, 5, 1, 0} |
| Clustal Omega | Number of combined iterations = {0, 1, 2, 3, 4, 5} |
| Coffee | Default |
| MUSCLE | Default |
| MAFFT | Default |
| BWA | K = 14, W = 20, r = 10, A = 1, B = 1, O = 1, E = 1, L = 0 |
| MATLAB® | Position of reads in the SAM file is less than or equal to = {1, 8, 15} |

At block 1008, the method 1000 may include performing a first consensus procedure over the aligned data sequences of the first group of nucleotide sequence blocks to produce a first output nucleotide data sequence. The means for performing the first consensus procedure may be a computing device. The computing device may segment each aligned sequence into maximal length homopolymer segments. The computing device, starting from the base immediately fol- The alignment is divided into 18 non-overlapping segments corresponding to different maximal length homopolymers. The segments may have different lengths, but due to the balancing constraint, no segment has length exceeding 8. To improve the current estimate $C_p$, a consensus is formed, starting from the left, by adding a new homopolymer at each step. Because the first three homopolymer segments ($r_1$-$r_3$) have lengths consistent across all sequences, and do not violate the balancing property, the new consensus sequence (cns) begins:

cns                TTCA.

Next, a homopolymer corresponding to the forth segment ($r_4$) is added. According to the four sequences, this homopolymer should have a length of either 3 or 4 (the sequences in question are CCC or CCCC). Note that the majority rule suggests that the correct sequence is CCC; this sequence also satisfies the balancing property, because the next symbol, from the fifth segment, is A. The second option, CCCC, does not satisfy the balancing property. Hence, the only valid solution to this point is:

cns                TTCACCC.

For the fifth segment, the majority rule suggests that the correct sequence is of the next homopolymer is AAAA. Also, it is apparent that at least four G or C symbols must be present in both segments $r_6$ and $r_7$; otherwise the resulting block does not have a balanced G-C content. The only homopolymer choices that satisfy these constraints are CCC for $r_6$ and G for $r_7$. Because all the homopolymer sequences for segments $r_8$ to $r_{12}$ have lengths consistent across all sequences, the 24 symbols of the consensus read as TTCAC-CCAAAACCCGAAAACCGCT (SEQ ID NO:46). Notably, the last 8 symbols do not have a balanced GC composition. Because the first encountered ambiguity in the consensus procedure came from segment $r_5$, the homopolymer is changed to AAAAA instead of AAAA, even though it contradicts the majority choice. Then, the consensus through segment 14 is:

(SEQ ID NO: 47)
cns         TTCACCCAAAAACCCGAAAACCGCTTCA.

A violation of the majority rules as described above is rare, and is included only for illustrative purposes. In the final step, the homopolymer G is selected for segment $r_{15}$, although it again violates the majority rule—any other choice would result in a consensus sequence with 31 symbols, a length not divisible by 8. Accordingly, the first output nucleotide data sequence is:

(SEQ ID NO: 48)
cns         TTCACCCAAAAACCCGAAAACCGCTTCAGCGA which satisfies the G-C-balanced property.

At block 1010, the method 1000 may include determining that at least one fixed-length substring of the first output nucleotide data sequence does not have 50% G-C and 50% A-T. In some embodiments, the first output nucleotide sequence matches the target nucleotide data sequence. In other embodiments, at least one fixed-length substring of the first output nucleotide data sequence does not have 50% G-C and 50% A-T.

At block 1012, the method 1000 may include, in response to determining that at least one fixed-length substring of the first output nucleotide data sequence does not have 50% G-C and 50% A-T, selecting a second group of the nucleotide sequence blocks read from the nanopore-based storage device. The second group of the nucleotide sequence blocks may each have address sequences with exactly one deletion, insertion, or substitution error. The means for selecting may be a computing device.

At block 1014, the method 1000 may include aligning the data sequences from the first group and the second group of the nucleotide sequence blocks with one another to provide a second output nucleotide data sequence. The computing device may perform a more multiple sequence alignments, using MSA algorithms such as Kalign, Clustal Omega, Coffee, MUSCLE, MAFFT, BWA, MATLAB®, etc. The computing device may further align the fixed output nucleotide data sequence with the data sequences from the first group and the second group of nucleotide sequence blocks.

At block 1016, the method 1000 may include a performing a second consensus procedure over the aligned data sequences of the aligned data sequences of the first group and the second group of nucleotide sequence blocks to produce a second output nucleotide data sequence. The computing device may segment each aligned sequence into maximal length homopolymer segments. The means for performing the first consensus procedure may be a computing device. The computing device, starting from the base immediately following the address sequence (e.g., from the left), may select for each segment a majority homopolymer length. The computing device may further determine whether, for a majority homopolymer length, each fixed-length substring of the data sequence has 50% G-C and 50% A-T, and if not, select a non-majority homopolymer length instead. The computing device may further determine whether, for a majority homopolymer length, the total length of the data sequence is evenly divisible by the length of the fixed-length substring, and if not, select a non-majority homopolymer length instead.

At block 1018, the method 1000 may include determining that at least one of the fixed-length substrings of the second output nucleotide data sequence does not have 50% G-C and 50% A-T. In some embodiments, the second output nucleotide sequence matches the target nucleotide data sequence. In other embodiments, at least one of the fixed-length substrings of the second output nucleotide data sequence does not have 50% G-C and 50% A-T.

The method 1000 may include, in response to determining that at least one of the fixed-length substrings of the second output nucleotide data sequence does not have 50% G-C and 50% A-T, additional blocks equivalent to 1012, 1014, 1016, and 1018, e.g., for selecting and aligning a third group of the nucleotide sequence blocks read from the nanopore-based storage device, performing a consensus procedure, and determining if a third output nucleotide data sequence has 50% G-C and 50% A-T, etc., for any of a number of additional iterations.

In one example, the image-encoded codeword blocks, encoded and written as described above, were mixed in equimolar concentration. One microgram of pooled DNA blocks was used to construct the nanopore-based storage device library. The DNA block libraries were pooled and sequenced for 48 hours in a portable size nanopore-based sequencer. All of the reads used in subsequent testing were generated within the first 12 hours of sequencing. Base-calling was performed in real time with a cloud service; the run produced a total of 6,660 reads that passed the filter. The sequencing error rate was 12%.

A preliminary consensus sequence of a first group of nucleotide sequence blocks, each having an address sequence without any deletion, insertion, or substitution errors, was produced by determining a "majority homopolymer" of consensus sequences from the Kalign, Clustal Omega, Coffee, and MUSCLE MSA algorithms. The preliminary consensus sequence and the first group of nucleotide sequence blocks were aligned using a BWA MSA algorithm (see, e.g., FIG. 8), and a consensus procedure over the data sequences of the aligned nucleotide sequence blocks was performed as described above, providing a first output nucleotide data sequence. A second group of nucleotide sequence blocks, each having an address sequence with exactly one deletion, insertion, or substitution error, was selected. The first output nucleotide data sequence and the first and second groups of nucleotide sequence blocks were aligned using a BWA MSA algorithm. A consensus procedure over the data sequences of the aligned nucleotide sequence blocks was performed as described above, producing a second output nucleotide data sequence with an error rate of only 0.02% (without any error-correction redundancy), as shown in Table 3, below.

TABLE 3

Number of read errors at two rounds
of iterative anchored alignment.

| DNA blocks (length in bp) | Errors after First Alignment | Errors after Second Alignment |
|---|---|---|
| 1 (1,000) | 9 deletions | 2 deletions |
| 2 (1,000) | 7 deletions | None |
| 3 (1,000) | 3 deletions | None |
| 4 (1,000) | 1 deletion | None |
| 5 (1,000) | None | None |
| 6 (1,000) | 1 deletion | None |
| 7 (1,000) | 2 deletions | None |
| 8 (1,000) | None | None |
| 9 (1,000) | 2 deletions | None |
| 10 (1,000) | None | None |
| 11 (1,000) | None | None |
| 12 (1,000) | 1 deletion | None |
| 13 (1,000) | 1 deletion | None |
| 14 (1,000) | 1 deletion | None |
| 15 (1,000) | None | None |
| 16 (1,000) | 4 deletions | 1 deletion |
| 17 (880) | None | None |

Accordingly, the low-error sequencing methods described herein tends to significantly limit the number of errors, which errors tend to be exclusively deletions. In sequencing the image-encoded nucleotide data blocks, only three deletion errors were encountered throughout the whole encoded file. All deletions were confined to homopolymers of length at least five, and exclusively included As. Accordingly, the information about homopolymer symbols was recovered correctly.

In either alignment iteration, less than 200 reads per nucleotide data sequence were used. Such a small number of reads may be generated in a relatively short time, and it appears that, generally, higher quality reads are generated early. Accordingly, the readout cost and delay of portable, nanopore-based systems are highly competitive with those of other technologies.

In some embodiments, deletion errors in homopolymers of length exceeding one (e.g., errors remaining after blocks 1002-1018 of method 1000; see, FIG. 10) are corrected with homopolymer parity-check coding. Homopolymer parity-check coding may involve an error-correction scheme that parses the consensus sequence into homopolymers. As an example, parsing the sequence AATCCCGA into homopolymers AA, T, CCC, G, A provides a homopolymer length sequence of 2,1,3,1,1. Special redundancy that protects against asymmetric substitution errors is incorporated into the homopolymer length sequence. For example, if two deletions in the example consensus provided the sequence ATCCGA, the homopolymer length sequence would be 1,1,2,1,1. The original length sequence 2,1,3,1,1 can be recovered from 1,1,2,1,1 by correcting two bounded magnitude substitution errors, where the sequence of the homopolymer symbols is known from the consensus.

An example deletion correcting code leveraging the so-called "integer sequence" of an information sequence is as follows:

To correct t deletions that preserve homopolymer symbols, the encoding scheme requires approximately $t \log_2 N$ bits of redundancy, where N denotes the length of the encoded information sequence. Furthermore, the code partitions the space $\mathbb{F}_4^N$ and hence lends itself to systematic encoding, which is desirable when constructing codes compatible with different nanopore sequencers. The proposed construction outperforms existing general multiple deletion correcting codes, as it is adapted to the nanopore channel at hand.

For a vector $x \in \mathbb{F}_4^N$, the integer sequence of x is the sequence of lengths of maximal runs in x. For example, the integer sequence of x=(0,0,1,3,3,2,1,1) is $I(x)=(2,1,2,1,2)$ Similarly, the integer sequence of AATTTGCGAA (SEQ ID NO:50) equals (2,3,1,1,1,2). In the context of DNA coding, such a sequence is referred to as the homopolymer length sequence. The string sequence of a codeword represents the symbols in the maximal runs of x. For example, the string sequence of x equals $S(x)=(0,1,3,2,1)$ because the first run in x has value 0, the next run has value 1 and so on. The string sequence of AATTTGCGAA (SEQ ID NO:50) equals (A,T,G,C,G,A).

It is straightforward to see that one can uniquely recover x given its integer sequence and string sequence. In shorthand, $M(I(x), S(x))$ is used to denote the "reconstruction map", a map such that $M(I(x),S(x))=x$ Suppose that $z \in \mathbb{F}_2^N$, i.e., that z is a binary vector of length N. Then, let $\mathcal{B}_t(z)=\{z+e\}$, where $e \in \{0,-1\}^N$ and e has at most t non-zero components. Given I, S, and $\mathcal{B}_t$, the types of errors to be corrected can be defined, referred to here as sticky deletions, a special case of the general family of repetition errors.

Let $x \in \mathbb{F}_4^N$. Assume that $y \in \mathbb{F}_4^{N-s}$ (where s≤t) is such that $S(y)=S(x)$, and $I(y) \in \mathcal{B}_t(I(x))$.

The first condition enforces that deletions occurring in x leading to y can never cause runs to be added or removed. In other words, the deletions are not allowed to change the string sequence. The second restriction enforces that deletions occurring in x can cause each run length in x to decrease by at most one.

A code $\mathcal{C}(N, t)$, capable of correcting sticky deletions, is defined. For $x \in \mathbb{F}_4^N$, let |x| denote the number of runs in x. Assume that for |x|=r, where r<N, the output of I(x) has length N with the last N−r components of I(x) set to zero.

Suppose that $\mathcal{C}_H(N, t)$ is a binary code of length N capable of correcting up to t substitution errors. Let $\mathcal{C}(N, t) \subseteq \mathbb{F}_4^N$ be defined so that $\mathcal{C}(N,t)=\{x \in \mathbb{F}_4^N : I(x) \bmod 2 \in \mathcal{C}_H(N,t)\}$.

Let $\mathcal{D}_t$ denote a decoder for $\mathcal{C}_H(N, t)$ where if $y=z+e^{(2)} \in \mathbb{F}_2^N$, $z \in \mathcal{C}_H(N, t)$, and $e^{(2)} \in \mathbb{F}_2^N$ has at most t non-zero components, then $\mathcal{D}_t(y)=z$. The code $\mathcal{C}(N, t)$ can correct up to t sticky deletions:

The result may be proven by outlining the decoding algorithm. Suppose that the vector $x \in \mathcal{C}(N,t)$ is stored and that the vector $y \in \mathbb{F}_4^{N-s}$ is retrieved, where s≤t is the result of s sticky deletions.

First, compute $S=S(y)$. Because y is the result of at most t sticky deletions, $S=S(x)$. Next, I(x) may be recovered. Since y is the result of at most t sticky deletions occurring to x, $I(y) \in \mathcal{B}_t(I(x))$, $I(y)=I(x)+e$, where e has at most t non-zero components and each component has value −1. Notice that $I(y) \bmod 2 = (I(x)+e) \bmod 2 = I(x) \bmod 2 + e \bmod 2$ where $I(x) \bmod 2 \in \mathcal{C}_H(N, t)$ and e is a binary vector with at most t non-zero components. Therefore, applying $\mathcal{D}_t$ to $I(y) \bmod 2$ gives $$\mathcal{D}_t(I(y) \bmod 2) = \mathcal{D}_t(I(x) \bmod 2 + e \bmod 2) = I(x) \bmod 2.$$

From the previous equation, given $I(x) \bmod 2$, $e \bmod 2$ can be determined. Notice that every non-zero component at position $i$ in $e \bmod 2$ is the result of a sticky deletion. Therefore, the value of $I(y)$ at position $i$ is incremented by one to obtain $I(x)$. Using the map M, $x = M(I(x), S)$.

Note that the construction in Theorem 1 is not systematic. The scheme may be used to perform systematic encoding. Consider the case where $t=2$, and use a primitive BCH code over $\mathbb{F}_2$ of length 1023 and dimension 1003, shortened on the last 23 bits. The resulting code has length 1000, dimension 980, and can correct up to 2 random substitution errors. This code is denoted $C(1000,980,2)$. Since $C(1000,980,2)$ is a linear code, there exists a systematic encoder for $\mathcal{C}_H$, denoted Enc, that given an input $w \in \mathbb{F}_2^{980}$, outputs 20 parity bits such that $(w, \text{Enc}(w)) \in C(1000,980,2)$.

The information sequence, denoted by $M_4 \in \mathbb{F}_4^{980}$, is encoded into a codeword $x \in \mathbb{F}_4^{1000}$ according to the following procedure:

Set the first 980 symbols of $x$ to be equal to $M_4$ and let $= \text{Enc}(I(M_4)) \in \mathbb{F}_2^{20}$.

Convert $z$ to a quaternary representation and denote the resulting sequence with $z^{(4)} \in \mathbb{F}_4^{10}$.

$$\text{Set}(x_{983}, x_{984}, x_{985}, \ldots, x_{1000}) = z_1^{(4)}, z_1^{(4)}, z_2^{(4)}, z_2^{(4)}, \ldots, z_{10}^{(4)}, z_{10}^{(4)})$$

Note that since $z$ is binary, it follows that 10 symbols over $\mathbb{F}_4$ suffice to store $z$. Observe also that the last 20 symbols in $x$ arise by simply repeating every symbol in $z^{(4)}$ twice. Hence, it is straightforward to prove the following corollary.

Suppose $x$ is encoded according to the previous procedure and $y$ is the result of up to 2 sticky deletions in $x$. Then, it is possible to recover $x$ from $y$:

Let $v$ equal the last 20 symbols in $y$ read in reverse order. In other words, the first symbol of $v$ equals the last symbol in $y$, the second symbol in $v$ equals the second to last symbol in $y$, and so on. Let $z_R$ be equal to the last 20 symbols in $x$ (which results from repeating every symbol in $z^{(4)}$, generated by the encoding procedure) read in reverse order. It is possible to recover $z_R$ from $v$ given that at most 2 sticky deletions occurred in the string[1]. Note that if $z_R$ is known, one can easily recover the parity bits $z$ and combine the parity bits (which have no errors) with the information symbols in $x$ to construct a vector $\hat{y} \in \mathfrak{B}_{32}(x)$, where $\hat{y}$ has at most 2 sticky deletions in the information symbols and $x \in \mathcal{CC}(N, t)$.

Consider the sequences $\mathbf{1}(v) = (u_1, u_2, \ldots, u_{|v|})$, $I(z_R) = (s_1, s_2, \ldots, s_{|z_R|})$, and $S(v)$. As a consequence of the sticky channel definition, $S(v) = S(z_R)$. Note also that for every symbol $u_i \in I(v)$, there is $u_i \in \{s_i, s_i - 1\}$. As a result of the encoding, $s_i \equiv 0 \bmod 2$. Therefore, $s_i$ can be recovered from $u_i$ by setting $u_i = u_i + 1$ if $u_i \equiv 1 \bmod 2$ and setting $u_i = u_i$ otherwise. In this manner, $I(z_R)$ can be recovered, and $z_R$ can be determined from $M(I(z_R), S(z_R))$.

As an example, the homopolymer parity-check coding was applied to the second output nucleotide data sequence read from the image-encoded codeword blocks described above. The rate of the homopolymer check codes was 0.95, and it allowed for systematic encoding, which cannot be achieved via simple $(d=1, k=6)$ run-length-constrained code of slightly higher rate 0.998. Furthermore, the homopolymer parity checks may be stored on classical media which have negligible small error probabilities to further increase the code rate to 0.98. This comes at almost no additional cost, as the homopolymer checks constitute less than 0.02% of the data volume.

The homopolymer parity-check coding corrected the three errors remaining in the 17 codewords, thereby producing error-free reconstructed images. See FIG. 11. The images reconstructed with and without homopolymer checks are shown in FIG. 12.

In some embodiments, a low-error sequencer includes a nanopore-based storage device storing a plurality of nucleotide sequence blocks. In some embodiments, each of the nucleotide sequence blocks contains respective address sequences followed by data sequences. In some embodiments, each of the data sequences as stored is identical to that of a target nucleotide data sequence. In some embodiments, each of the data sequences contains a series of fixed-length substrings and each of the fixed-length substrings is 50% guanine and cytosine and 50% adenine and thymine. In some embodiments, reading form the nanopore-based storage device introduces deletion, insertion, or substitution errors into the nucleotide sequence blocks. In some embodiments, the low-error sequence system includes a computing device including a memory storing program instructions that, upon execution by a processor, cause the computing device to perform operations. In some embodiments, the operations include obtaining the plurality of nucleotide sequence blocks read from the nanopore-based storage device. In some embodiments, the operations include selecting a first group of the nucleotide sequence blocks, each having address sequences without any deletion, insertion, or substitution errors. In some embodiments, the operations include aligning the data sequences from the first group of nucleotide sequence blocks with one another. In some embodiments, the operations include performing a first consensus procedure over respective aligned nucleotides of the data sequence from the first group of nucleotide sequence blocks, wherein the first consensus procedure produces a first output nucleotide data sequence.

In some embodiments, the first output nucleotide data sequence matches the target nucleotide data sequence.

In some embodiments, the operations further include determining that at least one fixed-length substring of the first output nucleotide data sequence is not 50% guanine and cytosine and 50% adenine and thymine. In some embodiments, in response to determining that at least one fixed-length substring of the first output nucleotide data sequence is not 50% guanine and cytosine and 50% adenine and thymine, selecting a second group of the nucleotide sequence blocks, each having address sequences with exactly one deletion, insertion, or substitution error. In some embodiments, the operations further include aligning the data sequences from the first group of nucleotide sequence blocks and the data sequences form the second group of nucleotide sequence blocks with one another. In some embodiments, the operations further include performing a second consensus procedure over respective aligned nucleotides of the data sequences from the first group of nucleotide sequence blocks and the data sequences from the second group of nucleotide sequence blocks, wherein the second consensus procedure produces a second output nucleotide data sequence.

In some embodiments, the second output nucleotide data sequence matches the target nucleotide data sequence.

In some embodiments, each of the fixed-length substrings contains run length values for runs of one or more consecutive nucleotides therein. In some embodiments, the consensus procedure determines deletion, insertion, or substitution errors in the fixed-length substrings of the data sequence based on inconsistencies between a number of consecutive nucleotides and an associated run length value.

In some embodiments, the consensus procedure determines deletion, insertion, or substitution errors in the data sequences based on a per-nucleotide majority-rule protocol that operates such that the fixed-length substrings of the first output nucleotides data sequence have 50% guanine and cytosine and 50% adenine and thymine.

In some embodiments, a low-error sequencer includes a non-transitory computer-readable medium, having stored thereon program instructions that, upon execution by a computing device, cause the computing device to perform operations. In some embodiments the operations include obtaining, from a nanopore-based storage device, a plurality of nucleotide sequence blocks. In some embodiments, each of the data sequences as stored in the nanopore-based storage device contains respective address sequences followed by data sequences. In some embodiments, each of the data sequences as stored is identical to that of a target nucleotide data sequence. In some embodiments, each of the data sequences contains a series of fixed-length substrings and each of the fixed-length substrings is 50% guanine and cytoside and 50% adenine and thymine. In some embodiments, reading from the nanopore-based storage device introduces deletion, insertion or substitution errors into the nucleotide sequence blocks. In some embodiments, the operations include selecting a first group of the nucleotide sequence blocks, each having address sequences without any deletion, insertion, or substitution errors. In some embodiments, the operations include aligning the data sequences from the first group of nucleotides sequence blocks with one another. In some embodiments, the operations include performing a consensus procedure over respective aligned nucleotides of the data sequences from the first group of nucleotide sequence blocks, wherein the consensus procedure produces a first output nucleotide sequence.

Information Rate and Data Storage Density

The information rate of a code (also known as the code rate) is the proportion of the stored data that represents useful information (i.e., is non-redundant). That is, if the code rate equals k/n, for every k bits of useful information, the code generates a total of n bits of data, of which n-k are redundant. In the data storage system, there is three layers of data encoding. The overall information rate is obtained by calculating the information rate for each layer and multiplying the results of the three layers.

In one encoding example, G-C-balanced DNA fragments of length 8 are used to store data. Note that the total number of GC-balanced DNA string of length 8 is $\binom{8}{4} \times 2^8$. Hence, the information rate of the balancing code is $$R_1 = \frac{\log_2\left[\binom{8}{4} \times 2^8\right]}{\log_2 4^8} = 0.8831. \tag{5}$$

Note that the nominator is the logarithm of the number of bits required to represent each GC-balanced DNA string of length 8.

In the example, each DNA block of length 1,000 bp is formed by concatenating an address sequence with the balanced blocks. Here, only 984 bp are used to store useful data while the remaining 16 bp are reserved for addressing. Accordingly, the information rate of this stage is $$R_2 = 987/1000 = 0.984. \tag{6}$$

In the example, homopolymer parity-check coding is included. Here, the code rate equals $$R_3 = 0.95. \tag{7}$$

The total information rate is obtained by multiplying the three rates from 5, 6 and 7, providing $$R = \text{Information rate} = 0.8831 \times 0.984 \times 0.95\ 0.83. \tag{8}$$

To calculate the DNA information density of the example, the average weight of a DNA base pair, 650 daltons (1 dalton equals the mass of a single hydrogen atom, or $1.67 \times 10^{-24}$ grams[33]), is used. because the example mapped 3,633 bytes of compressed data into 17 DNA blocks with total number of 16,880 bp, the DNA information density is:

$$\frac{3{,}633\ (B)}{16{,}880\ (bp)} \times \frac{1\ (bp)}{650 \times 1.67 \times 10^{-21}(g)} \approx 1.9827 \times 10^{20}\left(\frac{\text{byte}}{\text{gram}}\right).$$

These are the highest known achievable information rate and density of all DNA-based data storage systems to inventors knowledge, even when taking into account systems that do not use addressing or rely on highly accurate, but large volume laboratory sequencers.

CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

The invention claimed is:

1. A method for enabling portable readout of synthetic nucleotide sequences, the method comprising:

reading, from a nanopore-based storage device, a plurality of nucleotide sequence blocks, wherein each of the nucleotide sequence blocks as stored in the nanopore-based storage device contains respective address sequences followed by data sequences, wherein each of the data sequences as stored is identical to that of a target nucleotide data sequence, wherein each of the data sequences contains a series of fixed-length substrings and each of the fixed-length substrings is 50% guanine and cytosine and 50% adenine and thymine, and wherein the reading introduces deletion, insertion, or substitution errors into the nucleotide sequence blocks;

selecting, by a computing device, a first group of the nucleotide sequence blocks read from the nanopore-based storage device, each having address sequences without any deletion, insertion, or substitution errors;

aligning, by the computing device, the data sequences from the first group of nucleotide sequence blocks with one another; and performing, by the computing device, a first consensus procedure over respective aligned nucleotides of the data sequences from the first group of nucleotide sequence blocks, wherein the first consensus procedure produces a first output nucleotide data sequence.

2. The method of claim 1, wherein the first output nucleotide data sequence matches the target nucleotide data sequence.

3. The method of claim 1, further comprising:

determining that at least one fixed-length substring of the first output nucleotide data sequence is not 50% guanine and cytosine and 50% adenine and thymine;

in response to determining that at least one fixed-length substring of the first output nucleotide data sequence is not 50% guanine and cytosine and 50% adenine and thymine, selecting a second group of the nucleotide sequence blocks read from the nanopore-based storage device, each having address sequences with exactly one deletion, insertion, or substitution error;

aligning the data sequences from the first group of nucleotide sequence blocks and the data sequences from the second group of nucleotide sequence blocks with one another; and performing a second consensus procedure over respective aligned nucleotides of the data sequences from the first group of nucleotide sequence blocks and the data sequences from the second group of nucleotide sequence blocks, wherein the second consensus procedure produces a second output nucleotide data sequence.

4. The method of claim 3, wherein the second output nucleotide data sequence matches the target nucleotide data sequence.

5. The method of claim 1, wherein each of the fixed-length substrings consists of 8 nucleotides.

6. The method of claim 1, wherein each of the fixed-length substrings contains run length values for runs of one or more consecutive nucleotides therein.

7. The method of claim 6, wherein the consensus procedure determines deletion, insertion, or substitution errors in the fixed-length substrings of the data sequences based on inconsistencies between a number of consecutive nucleotides and an associated run length value.

8. The method of claim 1, wherein the consensus procedure determines the first output nucleotide data sequence from the data sequences based on a per-nucleotide majority-rule protocol that operates such that the fixed-length substrings of the first output nucleotide data sequence have 50% guanine and cytosine and 50% adenine and thymine.

9. The method of claim 1, wherein each of the address sequences is 8-32 nucleotides in length, and wherein each of the data sequences is 512-2048 nucleotides in length.

10. The method of claim 1, wherein each of the address sequences is p nucleotides in length, and wherein a particular address sequence of the address sequences does not appear as a non-address substring in any of the nucleotide sequence blocks.

11. The method of claim 1, wherein each of the address sequences is p nucleotides in length, and wherein each of the address sequences is a Hamming distance of at least p/2 from one another.

12. The method of claim 1, wherein each of the address sequences is 50% guanine and cytosine and 50% adenine and thymine.

13. A system comprising:
a nanopore-based storage device storing a plurality of nucleotide sequence blocks, wherein each of the nucleotide sequence blocks contains respective address sequences followed by data sequences, wherein each of the data sequences as stored is identical to that of a target nucleotide data sequence, wherein each of the data sequences contains a series of fixed-length substrings and each of the fixed-length substrings is 50% guanine and cytosine and 50% adenine and thymine, and wherein reading from the nanopore-based storage device introduces deletion, insertion, or substitution errors into the nucleotide sequence blocks; and
a computing device including a memory storing program instructions that, upon execution by a processor, cause the computing device to perform operations comprising:
obtaining the plurality of nucleotide sequence blocks read from the nanopore-based storage device;
selecting a first group of the nucleotide sequence blocks, each having address sequences without any deletion, insertion, or substitution errors;
aligning the data sequences from the first group of nucleotide sequence blocks with one another; and
performing a first consensus procedure over respective aligned nucleotides of the data sequences from the first group of nucleotide sequence blocks, wherein the first consensus procedure produces a first output nucleotide data sequence.

14. The system of claim 13, wherein the first output nucleotide data sequence matches the target nucleotide data sequence.

15. The system of claim 13, the operations further comprising:
determining that at least one fixed-length substring of the first output nucleotide data sequence is not 50% guanine and cytosine and 50% adenine and thymine;
in response to determining that at least one fixed-length substring of the first output nucleotide data sequence is not 50% guanine and cytosine and 50% adenine and thymine, selecting a second group of the nucleotide sequence blocks, each having address sequences with exactly one deletion, insertion, or substitution error;
aligning the data sequences from the first group of nucleotide sequence blocks and the data sequences from the second group of nucleotide sequence blocks with one another; and
performing a second consensus procedure over respective aligned nucleotides of the data sequences from the first group of nucleotide sequence blocks and the data sequences from the second group of nucleotide sequence blocks, wherein the second consensus procedure produces a second output nucleotide data sequence.

16. The system of claim 15, wherein the second output nucleotide data sequence matches the target nucleotide data sequence.

17. The system of claim 13, wherein each of the fixed-length substrings contains run length values for runs of one or more consecutive nucleotides therein.

18. The system of claim 17, wherein the consensus procedure determines deletion, insertion, or substitution errors in the fixed-length substrings of the data sequences based on inconsistencies between a number of consecutive nucleotides and an associated run length value.

19. The system of claim 13, wherein the consensus procedure determines deletion, insertion, or substitution errors in the data sequences based on a per-nucleotide majority-rule protocol that operates such that the fixed-length substrings of the first output nucleotide data sequence have 50% guanine and cytosine and 50% adenine and thymine.

20. An article of manufacture including a non-transitory computer-readable medium, having stored thereon program instructions that, upon execution by a computing device, cause the computing device to perform operations comprising:
obtaining, from a nanopore-based storage device, a plurality of nucleotide sequence blocks, wherein each of the nucleotide sequence blocks as stored in the nanopore-based storage device contains respective address sequences followed by data sequences, wherein each of the data sequences as stored is identical to that of a target nucleotide data sequence, wherein each of the data sequences contains a series of fixed-length substrings and each of the fixed-length substrings is 50% guanine and cytosine and 50% adenine and thymine, and wherein reading from the nanopore-based storage device introduces deletion, insertion, or substitution errors into the nucleotide sequence blocks;
selecting a first group of the nucleotide sequence blocks, each having address sequences without any deletion, insertion, or substitution errors;
aligning the data sequences from the first group of nucleotide sequence blocks with one another; and
performing a consensus procedure over respective aligned nucleotides of the data sequences from the first group of nucleotide sequence blocks, wherein the consensus procedure produces a first output nucleotide data sequence.

* * * * *

SEQUENCE LISTING

<160> NUMBER OF SEQ ID NOS: 50

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1
gtattgccag ag                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 2
tcccatgaga ga                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 3
acggccttct ta                                                          12

<210> SEQ ID NO 4
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 4
ggatcgccag cg                                                          12

```
<210> SEQ ID NO 5
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 5
ccgcgctggc ga                                                          12

<210> SEQ ID NO 6
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 6
tgcgcctccc gc                                                          12

<210> SEQ ID NO 7
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 7
cataccgtct tg                                                          12

<210> SEQ ID NO 8
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 8
gagaccgtca ta                                                          12

<210> SEQ ID NO 9
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 9
catagcgcca ta                                                          12

<210> SEQ ID NO 10
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 10
actactctca cg                                                          12

<210> SEQ ID NO 11
<211> LENGTH: 12
<212> TYPE: DNA
<213> ORGANISM: Artificial Sequence
<220> FEATURE:
<223> OTHER INFORMATION: Synthetic oligonucleotide
```

```
<400> SEQUENCE: 11
ctccactcat ag                                                        12

<210> SEQ ID NO 12
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 12
tactccaacc tg                                                        12

<210> SEQ ID NO 13

<400> SEQUENCE: 13

000

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cgtagtcagc gtgtcaatca                                                20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tgcacagtcg agctatcaca                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gactgactga tgacgactga                                                20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gctatatgcg agtcgagtca                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 18
gtacactcag catcgactca                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aattactaag cgaccttctc                                              20

<210> SEQ ID NO 20
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 20
tatgcgcgac cccct                                                   16

<210> SEQ ID NO 21
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 21
ccgaatatca aaaatc                                                  16

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 22
aatccgcgac ccccga                                                  16

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 23
cccaatatca aaatag                                                  16

<210> SEQ ID NO 24
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 24
aaaccgcgac cccgct                                                  16

<210> SEQ ID NO 25
<211> LENGTH: 16

```
<212> TYPE: DNA
<213> ORGANISM: Artificial Sequence
<220> FEATURE:
<223> OTHER INFORMATION: Synthetic oligonucleotide

<400> SEQUENCE: 25
gcctatatca aaattc                                                    16

<210> SEQ ID NO 26
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 26
taagcgcgac cccgga                                                    16

<210> SEQ ID NO 27
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 27
cgcaatatca aataac                                                    16

<210> SEQ ID NO 28
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 28
ataccgcgac ccgcca                                                    16

<210> SEQ ID NO 29
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 29
ggctatatca aatatg                                                    16

<210> SEQ ID NO 30
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 30
ttagcgcgac ccgcgt                                                    16

<210> SEQ ID NO 31
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 31
```
gggtatatca aattac 16

<210> SEQ ID NO 32
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 32
tttgcgcgac ccggca 16

<210> SEQ ID NO 33
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 33
cggaatatca aatttg 16

<210> SEQ ID NO 34
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 34
attccgcgac ccgggt 16

<210> SEQ ID NO 35
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 35
aaagcccctg cgccgt 16

<210> SEQ ID NO 36
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 36
aaagcccctg cgccgt 16

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 41
ttcacccaaa aacccgaaaa ccgcttcagc ga                          32

<210> SEQ ID NO 42
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 42
ttcaccccaa aaccgaaaac cgcttcacga                             30

<210> SEQ ID NO 43
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 43
ttcacccaaa aacccgaaaa ccgcttcagc ga                          32

<210> SEQ ID NO 44
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 44
ttcacccaaa aacccgaaaa ccgcttcagc ga                          32

<210> SEQ ID NO 45

<400> SEQUENCE: 45

000

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
ttcacccaaa acccgaaaac cgct                                   24

```
<210> SEQ ID NO 47
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 47
ttcacccaaa aacccgaaaa ccgcttca                                        28

<210> SEQ ID NO 48
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 48
ttcacccaaa aacccgaaaa ccgcttcagc ga                                   32

<210> SEQ ID NO 49

<400> SEQUENCE: 49

000

<210> SEQ ID NO 50
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 50
aatttgcgaa                                                            10
```